US006858605B2

(12) United States Patent
Sólyom et al.

(10) Patent No.: US 6,858,605 B2
(45) Date of Patent: Feb. 22, 2005

(54) SUBSTITUTED 2,3-BENZODIAZEPINE DERIVATIVES

(75) Inventors: Sándor Sólyom, Budapest (HU); Gizella Ábrahám, Budapest (HU); Tamás Hámori, Budapest (HU); Pál Berzsenyi, Budapest (HU); Ferenc Andrási, Budapest (HU); István Kurucz, Budapest (HU)

(73) Assignee: IVAX Drug Research Institute, Ltd., Budapest (HU)

( * ) Notice: Subject to any disclaimer, the term of this patent is extended or adjusted under 35 U.S.C. 154(b) by 0 days.

(21) Appl. No.: 10/358,053

(22) Filed: Feb. 4, 2003

(65) Prior Publication Data

US 2004/0152693 A1 Aug. 5, 2004

(51) Int. Cl.$^7$ .................... C07D 243/10; C07D 487/02; C07D 491/00; A61K 31/55

(52) U.S. Cl. ...................... 514/220; 514/221; 540/557; 540/567

(58) Field of Search .............................. 540/557, 567; 514/220, 221

(56) References Cited

U.S. PATENT DOCUMENTS

| | | | |
|---|---|---|---|
| 4,614,740 | A | 9/1986 | Láng et al. |
| 5,536,832 | A | 7/1996 | Andrási et al. |
| 5,756,495 | A | 5/1998 | Hámori et al. |
| 5,795,886 | A | 8/1998 | Anderson et al. |
| 6,200,970 | B1 | 3/2001 | Ling et al. |

FOREIGN PATENT DOCUMENTS

| | | |
|---|---|---|
| EP | 0 699 677 A1 | 3/1996 |
| GB | 2 311 779 A | 10/1997 |
| WO | 92/11262 A1 | 7/1992 |
| WO | 95/01357 A1 | 1/1995 |
| WO | 96/04283 A1 | 2/1996 |
| WO | 96/06606 A1 | 3/1996 |
| WO | 97/28135 A1 | 8/1997 |
| WO | 99/07707 A1 | 2/1999 |
| WO | 99/07708 A1 | 2/1999 |
| WO | 01/04122 A2 | 1/2001 |

OTHER PUBLICATIONS

Anderson et al. (Bioorganic & Medicinal Chemistry Letters 9 (1999), 1953–1956).*
Lipton et al., *The New England Journal of Medicine* 330, No. 9, pp. 613–622 (Mar. 3, 1994), published by the Massachusetts Medical Society, Boston, MA.
Goodman and Gilman's *The Pharmacological Basis of Therapeutics*, 10$^{th}$ edition (2001), p. 309, published by the McGraw–Hill Companies, Inc., New York, New York.
*Drugs of the Future 2001*, 26(8), pp. 754–756 (2001), published by Prous Science, Barcelona, Spain.

Konitsiotis et al., *Neurology* 54, No. 8, pp. 1589–1595 (Apr. 25, 2000), published by Lippincott Williams & Wilkins, Philadelphia, PA.
Chase et al., *J. Neurol.* 247 [Suppl. 2]: pp. II/36–II/42 (Apr. 2000), published by Steinkopfff Verlag, Darmstadt, Germany.
Belayev et al., *Journal of Neurotrauma*, vol. 18, No. 10, pp. 1031–1038, publsihed by Mary Ann Liebert, Inc., Larchmont, NY, 2001.
Vorwerk et al., *Survey of Ophthalmology*, vol. 43, Supplement 1, pp. S142–S150 (Jun. 1999), published by Elsevier Science Inc., New York, New York.
Mattson et al., *Nature*, vol. 382, pp. 674–675 (Aug. 1996), published by Macmillan Magazines Ltd., London, England.
Cacabelos et al., *Drugs of Today 2000*, 36(7), pp. 415–499 (2000), published by Prous Science, Barcelona, Spain.
Chappel et al., *Neurology* 58, No. 11, pp. 1680–1682 (Jun. 11, 2002), published by Lippincott Williams & Wilkins, Philadelphia, PA.
Rzeski et al., *PNAS*, vol. 98, No. 11, pp. 6372–6377 (May 22, 2001), published by the National Academy of Sciences, Washington, D.C.
Steinman, *Nature Medicine*, vol. 6, No. 1, pp. 15–16 (Jan. 2000), published by Nature Publishing Co., New York, New York.
Pitt et al., *Nature Medicine*, vol. 6, No. 1, pp. 67–70 (Jan. 2000) published by Nature Publishing Co., New York, New York.
Smith et al., *Nature Medicine*, vol. 6, No. 1, pp. 62–66 (Jan. 2000) published by Nature Publishing Co., New York, New York.
Akins et al., *Current Medical Research and Opinions*, vol. 18, Suppl. 2, pp. s9–s13 (2002), published by Librapharm Limited, Newbury, Berkshire UK.
Buchan et al., *Stroke* 24, No. 12 [Suppl I]: I–148–I–152 (Dec. 1993), published by Lippincott Williams & Watkins, Baltimore, MD.
Mysbros et al., *Annals New York Academy of Sciences*, 765, 262–271 (1995), published by New York Academy of Sciences, New York, New York.
Parsons et al., *Drug News Perspect.* 11(9), 523–569 (1998), published by Prous Science, S.A., Barcelona, Spain.
Bräuner–Osborne et al., *J. Med. Chem.*, vol. 43, No. 14, 2609–2645 (2000), published by American Chemical Society, Washington, D.C.

(List continued on next page.)

*Primary Examiner*—Bruck Kifle
(74) *Attorney, Agent, or Firm*—Michael A. Steinberg; Ivax Corporation

(57) ABSTRACT

The invention relates to new 2,3-benzodiazepine derivatives of formula (I), isomers and acid addition salts thereof and to pharmaceutical compositions containing the same, as well as to pharmaceutical compositions and methods of using the same suitable for treating conditions associated with muscle spasms, epilepsy, acute and chronic forms of neurodegenerative diseases as well as preventing, treating or alleviating the symptoms of acute and chronic inflammatory disorders.

19 Claims, No Drawings

OTHER PUBLICATIONS

Gill, *Cerebrovascular and Brain Metabolism Reviews*, 6, 225–256 (1994), published by Raven Press Publishers, New York, New York.

Meldrum, *Neurology*, 44, Suppl. 8, S14–S23 (1994), published by Advanstar Millennium, New York, New York.

Turski et al., *J. Pharmacol. Exp. Ther.*, vol. 260, No. 2, 742–747 (1992), published by Williams & Wilkins, Baltimore, MD.

Skerry et al., *Trends in Pharm. Sci.*, vol. 22, No. 4, 174–181 (2001), published by Elsevier Sciences London, London, UK.

Said, *Trends in Pharm. Sci.*, vol. 20, 132–135 (1999), published by Elsevier Sciences London, London, UK.

Said et al., *Trends in Pharm. Sci.*, vol. 22, No. 7, 344–345 (2001), published by Elsevier Sciences London, London, UK.

Visi et al., *CNS Drug Reviews*, vol. 2, No. 1, 99–126 (1996), published by Neva Press, Inc., Branford, CT.

Tarnawa et al., *European Journal of Pharmacology* 167, 193–199 (1989), published by Elsevier Science Publishers B.V., Amsterdam, The Netherlands.

Smith et al., *European Journal of Pharmacology* 187, 131–134 (1990), published by Elsevier Science Publishers B.V., Amsterdam, The Netherlands.

Ouardouz et al., *Neuroscience Letters* 125, 5–8 (1991), published by Elsevier Scientific Publishers Ireland Ltd., Ireland.

Donevan et al., *Neuron*, 10, 51–59 (1993), published by Cell Press, 50 Church Street, Cambridge, Massachusetts.

Smith et al., *Nature Medicine*, vol. 6, No. 1, 62–66 (2000), published by Nature America, Inc., New York, New York.

Nishizawa et al., *Advances in Experimental Medicine and Biology*, Vo. 462, *Advances in Bladder Research*, 275–281 (1999) published by Kluwer Academic/Plenum Publishers, New York, New York.

Bialer et al., *Epilepsy Research*, vol. 43, 11–58 (2001), published by Elsevier Science B.V., Amsterdam, The Netherlands.

Sheardown, *Brain Research*, 607, 189–194 (1993), published by Elsevier Science Publishers B.V., Amsterdam, The Netherlands.

Bleakman et al., *Neuropharmacology* vol. 35, No. 12, 1689–1702 (1996), published by Pergamon, Elsevier Science Ltd., Kidlington, UK.

Upton, *TiPS* 15, 456–462 (1994), published by Elsevier Sciences, London, UK.

Randall et al., *J. Pharmacol. Exp. Ther.*, 129, 163–171 (1960), published by Williams & Wilkins, Baltimore, MD.

Dunham et al., *J. Am. Pharm. Assoc.*, vol. 46, No. 3, 208–209 (1957), published by the American Pharmaceutical Association, Washington, D.C.

Bartus et al., *Stroke*, vol. 25, No. 11, 2265–2270 (1994), published by American Heart Association, Dallas, Texas.

Sydserff et al., *British Journal of Pharmacology*, vol. 114, 1631–1635 (1995), published by Stockton Press, New York, New York.

Steinman, *Nature Medicine*, vol. 6, No. 1, 15–16 (2000), published by Nature America Inc., New York, NY.

Werner et al., *J. Neurol. Transmiss. Suppl.*, 60, 375–385 (2000), published by Springer–Verlag/Wien, New York, New York.

Bjartmar et al., *Drugs of Today 2002*, 38(1), 17–29 (2002), published by Prous Science S.A., Barcelona, Spain.

Baker et al., *Nature*, vol. 404, 84–89 (2000), published by Nature Publishing Group, London, UK.

Gijbels et al., *J. Clin. Invest.* 94, 2177–2182 (1994), published by The Rockefeller University Press, New York, New York.

* cited by examiner

SUBSTITUTED 2,3-BENZODIAZEPINE DERIVATIVES

BACKGROUND OF THE INVENTION

1. Field of Invention

The invention relates to new 2,3-benzodiazepine derivatives substituted by heterocycles, the acid addition salts thereof, as well as the pharmaceutical compositions containing them. The invention also relates to the use of said compounds as AMPA receptor antagonists.

2. Summary of Related Art

Over-activation of glutamate receptors has been associated with several acute and chronic diseases of the central nervous system ("CNS"). Various glutamate receptor antagonists have been investigated as therapeutic modalities (see for example Parsons et al., *Drug News Perspect.* 11:523 (1998) and Brauner-Osborne et al., *J. Med. Chem.* 43:2609 (2000)).

AMPA (2-amino-3-(3-hydroxy-5-methyl-4-isoxazolyl)-propionic acid) type glutamate receptors play a major role in a variety of central nervous system disorders. Inhibition of the activation of AMPA type receptors has been shown to have neuroprotective, antiepileptic and muscle-relaxant effects (see e.g., *Cerebrouisc. Brain Metab. Rev* 6:225 (1994); *Neurology* 44 Suppl.8, S14 (1994); *J. Pharmacol Exp. Ther.* 260:742 (1992)).

Glutamate receptors have been found not only in the CNS but also in peripheral tissues indicating therapeutic potential opportunities beyond the CNS (see e.g., Skerry et al., *Trends in Pharm. Sci.*, Vol. 22, No. 4,174–181 (2001). Respiratory tract inflammation has been postulated to be benefically influenced by NMDA-type glutamate antagonists (Said, *Trends in Pharm. Sci.* 20:132 (1999); and Said et al., *Trends in Pharm. Sci.* 22:344 (2001)).

AMPA type receptors can be inhibited by various competitive and non-competitive antagonists. The therapeutic potential of non-competitive an agonists may be superior to that of competitive ones insofar as their activity is not dependent on high concentrations of endogenous glutamate (see e.g., Vizi et al., *CNS Drug Rev.*, 2:91 (1996)). One of the most prominent non-competitive AMPA receptor antagonists is 5-(4-aminophenyl)-8-methyl-9H-1,3-dioxolo[4,5-h][2,3]benzodiazepine (also designated as GYKI 52466) possessing remarkable antiepileptic, muscle relaxant and neuroprotective activities. (Tarnawa et al., *Eur. J. Pharmacol.*, 167:193 (1989); Smith, et al., *Eur. J. Pharmacol.*, 187:131 (1990); Ouardouz et al., *Neurosci. Lett.*, 125:5 (1991); Donevan et al., *Neuron*, 10:51 (993)).

Several non-competitive AMPA antagonists have been described in the literature including 3,4-dihydro-5H- or 4,5-dihydro-3H-2,3-benzodiazepines, containing an acyl group at position 3 of the ring (see e.g., Hungarian Patent Nos. 206,719 B and 219,777 B, U.S. Pat. No. 5,536,832, European Patent Publication No. 0699 677 A1, and British Patent No. 2 311 779, as well as WO 96/04 283, WO 97/28 135, WO 99/07 707, WO 99/07 708 and WO 01/04 122). WO 96/06 606 (corresponding to U.S. Pat. No. 5,795,886) describes several 2,3-benzodiazepine derivatives having aryl and heteroaryl substituents (e.g., pyridyl, thienyl, furyl, phenyl, imidazolyl, benzimidazolyl, etc.) at C3.

The compounds listed above have been found to be particularly useful in diseases in which the over-function of the glutamate system can be detected. Such acute disorders of the CNS include for example stroke, brain ischemia, brain and spinal cord injuries, perinatal hypoxia, hypoglycemic nervous damage, et. Additional chronic illnesses in which selected AMPA antagonists can be applied include e.g., Alzheimer's disease, Huntington's disease, amyotrophic lateral sclerosis, AIDS-induced dementia, glaucoma, diabetic retinopathy as well as Parkinson's disease. Furthermore, enhanced activity of the glutamate system has also been shown in conditions associated with neural damage (e.g., epilepsy, migraine, urinary bladder incontinence, psychosis—anxiety, schizophrenia etc., drug-abuse, pathological pain, brain edema and tardive dyskinesia) implying an impressive therapeutic potential for AMPA antagonists.

Recently, experimental data suggested that selected AMPA antagonists have beneficial effect on the autoimmune encephalomyelitis elicited in rats, which is the accepted model of multiple sclerosis (Smith et al., *Nature Medicine* 6:62 (2000)). In addition, AMPA and NMDA receptors in the spinal cord have been implicated in the contraction of the bladder and the urethra, suggesting that AMPA antagonists may be useful in the treatment of urinary incontinence (Nishizawa et al., *Adv in Exp. Med. & Biol.* Vol. 462, 275 (1999)).

Two 2,3-benzodiazepine derivatives GYKI 52466 (supra), and (R)-7-eacetyl-5-(4-aminophenyl)-8,9-dihydro-8-methyl-7H-1,3-dioxolo[4,5-h][2,3]benzodiazepine (GYKI 53773, also known as Talampanel) were beneficial. The latter has proved to be active in clinical trials on epilepsy patients (Bialer et al., *Epilepsy Res.* 43:11 (2001)).

In addition, GYKI 52466 has been reported to inhibit growth of selected tumor cell types (colon adenocarcinoma, astrocytoma, breast carcinoma, lung carcinoma and neuroblastoma) (Rzeski et al., *Proc. Nat. Acad. Sci.* 98:6372 (2001)).

SUMMARY OF THE INVENTION

The invention relates to new 2,3-benzodiazepine derivatives of formula (I), isomers and acid addition salts thereof and to pharmaceutical compositions containing the same,

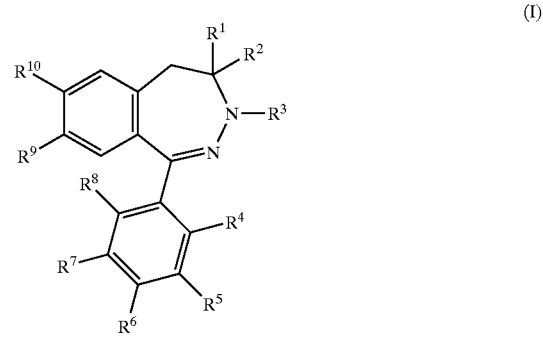

(I)

wherein the substituent meanings are as follows:

$R^1$ and $R^2$ independently of each other represent hydrogen atom or $C_1$–$C_3$ alkyl group, $R^3$ represents 5- or 6-membered, aromatic, saturated or partially saturated heterocyclic ring containing at least 2 hetero atoms, in which the hetero atom can be oxygen-, sulfur- or nitrogen atom and in the case when $R^3$ is a 5-membered ring one of the two heteroatoms is different from nitrogen;

$R^4$, $R^5$, $R^6$, $R^7$ and $R^8$ independently from each other represent hydrogen atom, halogen atom, $C_1$–$C_3$ alkyl group, nitro group or amino group, wherein the amino group can be substituted independently from each other with one or two $C_1$–$C_3$ alyl group, $C_2$–$C_5$ acyl group, or $C_2$–$C_5$alkoxycarbonyl group, or aminocarbonyl group, or $C_2$–$C_5$ alkylaminocarbonyl group, $R^9$ represents $C_1$–$C_3$ alkoxy group or halogen atom, $R^{10}$ represents hydrogen or halogen atom or $R^9$ and $R^{10}$ together can be $C_1$–$C_3$ alkylendioxy group.

Representative compounds include, without limitation, (R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine; (R)-5-(4-aminophenyl)-8-methyl-7-(5-methyl-1,3,4-thiadiazol-2-yl)-8,9-dihydro-7H-1,3-dioxolo[4,5-h][2,3] benzodiazepine; (R)-5-(4-aminophenyl)-8-methyl-7-(1,3,4-thiadiazol-2-yl)-8,9-dihydro-7H-1,3-dioxolo[4,5-h][2,3]benzodiazepine; (R)-5-(4-aminophenyl)-8-methyl-7-(2-thiazolyl)-8,9-dihydro-7H-1,3-dioxolo[4,5-h][2,3]benzodiazepine; (R)-5-(4-aminophenyl)-7-(4,5-dihydro-thiazol-2-yl)-8-methyl-8,9-dihydro-7H-1,3-dioxolo[4,5-h][2,3]benzodiazepine; (R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine; (R)-5-(4-aminophenyl)-8-methyl-7-(5-methyl-1,3,4-oxadiazol-2-yl)-8,9-dihydro-7H-1,3-dioxolo[4,5-h][2,3] benzodiazepine and the acid addition salts thereof.

The invention also discloses pharmaceutical compositions comprising a compound of formula (I) as the active ingredient, wherein the meaning of $R^1$–$R^{10}$ is as defined herein, or a steroisomer or a pharmaceutically acceptable salt thereof together with pharmaceutically acceptable solvents, diluents, carriers and filling materials.

The compounds are suitable for treating conditions associated with muscle spasms, epilepsy, acute and chronic forms of neurodegenerative diseases as well as preventing, treating or alleviating the symptoms of acute and chronic inflammatory disorders.

One of skill will appreciate, in light of the many publications relating to the expanding therapeutic values of AMPA type receptor antagonists, that the compounds of the invention are useful in a very large number of unrelated conditions.

Hence, methods for treating glutamate dysfunction associated with an acute or chronic neurodegenerative disease or in acute or chronic disease of the eyes associated with glutamate dysfunction are provided. Representative neurodegenerative disorders include, for example, cerebral ischemia (stroke), brain and spinal cord trauma, Alzheimer's disease, Huntington's disease, amyotrophic lateral sclerosis, AIDS-induced dementia, essential tremor, Parkinson's disease, multiple sclerosis and urinary incontinence. Acute or chronic disorders of the eyes associated with glutamate dysfunction include glaucoma or diabetic retinopathy. Disclosed also are methods for treating epilepsy, reducing muscle spasms, reducing pain, or inflammatory disorders which comprise administering to the subject in need of such treatment a therapeutically effective amount of the compounds of the invention. Included among the inflammatory disorders are allergic inflammatory disorders of the airways which can encompass allergic rhinitis, intrinsic or extrinsic asthma bronchiale, acute or chronic bronchitis, chronic obstructive pulmonary disease and pulmonary fibrosis.

DETAILED DESCRIPTION OF THE INVENTION

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

The invention discloses novel substituted 2,3-benzodiazepine derivative compounds and methods of making the same. Pharmaceutical compositions employing the novel substituted 2,3-benzodiazepine derivative compounds and their use for the treatment for a number of disease conditions are also disclosed.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Ginnan's *The Pharmacological Basis of Therapeutics,* 10th Ed., McGraw Hill Companies Inc., New York (2001). Anysuitable materials and/or methods known to those of skill can be utilized in carrying out the present invention. However, preferred materials and methods are described. Materials, reagents and the like to which reference is made in the following description and examples are obtainable from commercial sources, unless otherwise noted.

As used in this specification, the singular forms "a", "an" and "the" specifically also encompass the plural forms of the terms to which they refer, unless the content clearly dictates otherwise. For example, reference to "an antagonist" includes mixtures of antagonists.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or".

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

The methods of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

It will be understood that the subject to which a compound of the invention is administered need not suffer from a specific traumatic state. Indeed, the compounds of the invention may be administered prophylactically, prior to any development of symptoms. The term "therapeutic", "therapeutically", and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

The invention provides new 2,3-benzodiazepines of formula (I), the isomers as well as the acid addition salts thereof, wherein

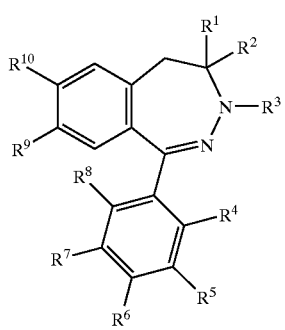

(I)

$R^1$ and $R^2$ independently of each other represent hydrogen atom or $C_1$–$C_3$ alyl group,
$R^3$ represents 5- or 6-membered, aromatic, saturated or partially saturated heterocyclic ring containing at least 2 hetero atoms, in which the hetero atom can be oxygen-, sulfur- or nitrogen atom and in the case when $R^3$ is a 5-membered ring one of the heteroatoms is different from nitrogen;
$R^4$, $R^5$, $R^6$, $R^7$ and $R^8$ independently from each other represent hydrogen atom, halogen atom, $C_1$–$C_3$ alyl group, nitro group or amino group, wherein the amino group can be substituted independently from each other with one or two $C_1$–$C_3$ alkyl group, $C_2$–$C_5$ acyl group, or $C_2$–$C_5$ alkoxycarbonyl group, or aminocarbonyl group, or $C_2$–$C_5$ alkylaminocarbonyl group,
$R^9$ represents $C_1$–$C_3$ alkoxy group or halogen atom,
$R^{10}$ represents hydrogen or halogen atom or
$R^9$ and $R^{10}$ together can be $C_1$–$C_3$ alkylendioxy group.

The meaning of alyl group encompasses both straight and branched chain alkyl groups. The meaning of alkenyl group can be vinyl, 1-propenyl or 2-propenyl group. The meaning of halogen atom can be fluorine, chlorine, bromine, or iodine atom. The amino group can be unsubstituted or substituted with one or two allyl groups, as well as acylated with aliphatic or aromatic carboxylic acid or any kind of carbonic acid esters.

The heterocyclic substituent of the benzodiazepine ring as $R^3$ can be, among others, a moiety selected from the group consisting of isoxazole, isothiazole, thiazole, thiazoline, 4-thiazolinone, oxazole, oxazoline, 1,3,4-thiadiazole, 1,3,4-thiadiazolin-2-one, 1,2,4-thiadiazolin-3-one, 1,4,2-oxathiazoline, 1,3,4-oxadiazole, 1,2,3-triazole, 1,3,4-triazole, tetrazole, pyridazine, pyrimidine, 1,3-thiazin-4-one and 1,3,4-thiadiazin-4-one ring.

In the case of compounds of formula (I), the term "isomers" means both enantiomers, as well as the E and Z isomers if applicable, furthermore, isomers shall include diastereomers, tautomers and mixture of them, for example racemic mixture.

Salts of the compounds of formula (I) relate to physiologically acceptable salts formed with inorganic or organic acids. Suitable inorganic acids can be, for example, hydrochloric acid, hydrobromic acid, phosphoric acid or sulfuric acid. Suitable organic acids can be, for example, formic acid, acetic acid, maleic and fumaric acid, succinic acid, lactic acid, tartaric acid, citric acid or methanesulfonic acid.

In one or more embodiment, the $R^3$ substituent is a 1,3,4-thiadiazol-2-yl, a 4,5-dihydro-thiazol-2-yl, a 2-thiazolyl or a 1,3,4-oxadiazolyl group, and an $R^5$ substituent is a hydrogen atom or methyl group, an $R^6$ substituent is an amino group, and $R^9$ and $R_{10}$ represent together a methylenedioxy group, or $R^9$ is a chlorine atom or methoxy group and $R_{10}$ is a hydrogen or chlorine atom.

One or more representative compounds of formula (I) of the invention are the following derivatives: (R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine; (R)-5-(4-aminophenyl)-8-methyl-7-(5-methyl-1,3,4-thiadiazol-2-yl)-8,9-dihydro-7H-1,3-dioxolo[4,5-h][2,3]benzodiazepine; (R)-5-(4-aminophenyl)-8-methyl-7-(1,3,4-thiadiazol-2-yl)-8,9-dihydro-7H-1,3-dioxolo[4,5-h][2,3]benzodiazepine; (R)-5-(4-aminophenyl)-8-methyl-7-(2-thiazolyl)-8,9-dihydro-7H-1,3-dioxolo[4,5-h][2,3]benzodiazepine; (R)-5-(4-aminophenyl)-7-(4,5-dihydro-thiazol-2-yl)-8-methyl-8,9-dihydro-7H-1,3-dioxolo[4,5-h][2,3]benzodiazepine; (R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine; (R)-5-(4-aminophenyl)-8-methyl-7-(5-methyl-1,3,4-oxadiazol-2-yl)-8,9-dihydro-7H-1,3-dioxolo[4,5-h][2,3]benzodiazepine; and the acid addition salts thereof.

The compounds of formula (I) can be prepared in the following way:
the heterocycle corresponding to the $R^3$ substituent is built up starting from a compound of

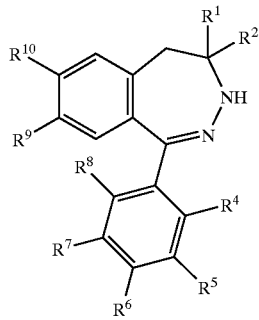

(II)

wherein the meaning of $R^1$, $R^2$, $R^4$, $R^5$, $R^6$, $R^7$, $R^8$, $R^9$ and $R^{10}$ is as defined above—by known methods, or a compound of formula (IV) or an isochromenllium salt of formula (IVa) which is formed from the compound of formula (IV)

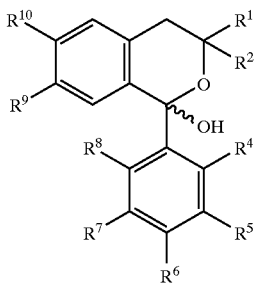

(IV)

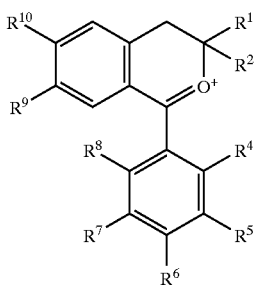

(IVa)

wherein the meaning of $R^1$, $R^2$, $R^4$, $R^5$, $R^6$, $R^7$, $R^8$, $R^9$ and $R^{10}$ is as defined above—is reacted with a compound of formula (V) or (VI)

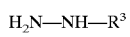 (V)

 (VI)

wherein the meaning of $R^3$ is as defined above and the meaning of $R^{11}$ is $C_2$–$C_8$ alkoxycarbonyl or aryl alkoxycarbonyl group—to obtain the compounds of formulas (VII) or (VIII).

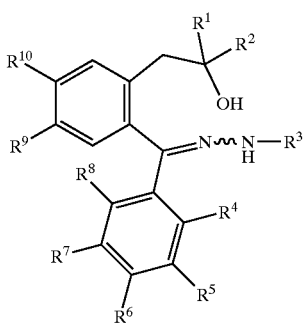

(VII)

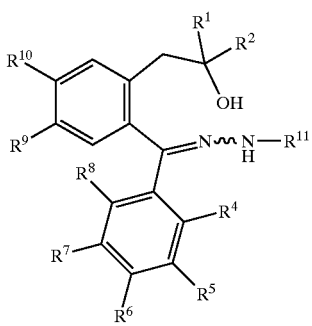

(VIII)

The hydroxyl group of the compounds of formulas (VII) or (VIII) is transformed into a sulfonate ester, and the latter intermediate is submitted to ring-closure resulting in compounds of formulas (I) or (III)

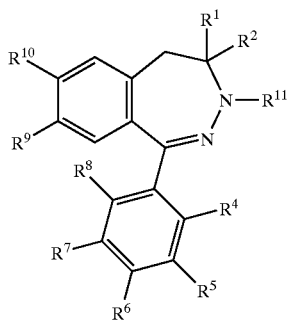

(III)

by applying a strong base. Alternatively, the compounds of formulas (VII) or (VIII) are transformed into compounds of formulas (I) or (III) according to Mitsunobu (*Synthesis*, I:1 (1988)). In the compound of formula (III), the $R^{11}$ group is cleaved to give the compound of formula (II), which is converted into the compound of formula (I) according to the method described in process a). Then, if desired, in a compound of formula (I) obtained according to any of the above processes, the nitro group is reduced or the amino group is acylated, alkylated, or after diazotation, is exchanged by a halogen atom or hydrogen atom, or a halogen atom is exchanged by an amino group and in this way it is transformed into another compound of formula (I) and/or the isomers are separated and, if desired, salts are formed.

The compounds of formula (II) are chiral compounds, and therefore formula (II) refers to either of the individual enantiomers or mixtures thereof. The heniketal type compounds of formula (IV) as well as the hydrazone derivatives of formulas (VII) and (VIII) represent different stereoisomers and they refer to all of the individual stereoisomers and mixtures thereof. The $R^{11}$ group can be a $C_2$–$C_8$ alkoxycarbonyl group, such as a tert-butoxycarbonyl or a benzyloxycarbonyl group.

The starting materials of formula (II) are known in the literature (U.S. Pat. No. 5,536,832 and British Patent No. 2,311,779, as well as WO 97/28 135 and WO 01/04 122). Hungarian Patent No. 219,777 and British Patent No. 2,311,779 describe the synthesis of optically active compounds of formula (II) as well.

The optically active compounds of formula (II) can be synthesized by reacting a hemiketal of formula (IV)—prepared for example from an optically active substituted phenyl-isopropanol according to Anderson et al. (*J. Am. Chem. Soc.* 117:12358 (1995))—with an alkoxycarbonyl-hydrazide containing an easily removable alkoxycarbonyl group, such as a tert-butoxy-carbamate in the presence of catalytic amount of an acid. The hydrazone of formula (VIII) obtained after isolation then is transformed into a mesyl ester e.g., with methanesulfonyl chloride in the presence of triethylamine, and the latter is treated with base, for example sodium hydroxide, in alcoholic solution to yield the benzo-diazepine derivative of formula (III) in a ring closure reaction. Then the substituent of the N-3 atom (numbering according to the benzodiazepine ring) is cleaved, e.g., by hydrolysis or another method, for example hydrogenolysis, to yield the desired compound of formula (II). The cleavage of the tert-butoxycarbonyl group may be carried out with trifluoroacetic acid or zinc bromide in dichloromethane.

The heterocyclic moiety—corresponding to the $R^3$ substituent—of the compound of formula (I) is synthesized starting from the compounds of formula (II) according to methods known in the art relating to heterocyclic chemistry.

Some of the compounds of formula (I) can be synthesized, for example, from the 4,5-dihydro-2,3-benzodiazepine derivatives substituted with thiocarbamoyl group at position 3 of the benzodiazepine ring. Latter compounds can be obtained from 4,5-dihydro-3H-2,3-benzodiazepine derivatives of formula (II), for example with potassium thiocyanate in acetic acid medium The thus-obtained 4,5-dihydro-3-thiocarbamoyl-3H-2,3-benzodiazepines are reacted with α-halo ketones or α-halo aldehyde acetals to yield 2,3-benzodiazepine derivatives having a substituted or unsubstituted 2-thiazolyl group. In an analogous reaction, if 2-halo carboxylic acid esters are used instead of the α-halo oxo-compound, the appropriate compounds containing a 3-thiazolinone ring are formed.

When the above-mentioned 4,5-dihydro-2,3-benzodiazepines containing thiocarbamoyl group in position 3 are reacted with β-halo carboxylic acid esters, for example ethyl 3-bromopropionate, then new 2,3-benzodiazepine derivatives substituted with 5,6-dihydro-[1,3]thiazin-4-one ring are obtained.

The compounds of formula (I) containing 1,3,4-thiadiazole group as $R^3$ substituent can be synthesized for example by the following way. First, a trimethylsilyl derivative is prepared from a 4,5-dihydro-3H-[2,3]benzodiazepine of formula (II), which is then reacted with thiophosgene to give thiocarboxylic acid chloride. Finally, the latter is treated with hydrazine to yield the thiocarboxylic acid hydrazide derivatives. The 2,3-benzodiazepine derivatives substituted with carbothiohydrazide group are reacted with an acid anhydride or chloride and the thus-obtained partially occurring ring closure of the carbothio-N-acylhydrazides is promoted by further acid treatment to yield [1,3,4]thiadiazolyl-2,3-benzodiazepines. Another procedure for the synthesis of the latter compounds is to react the above-mentioned intermediate thiocarboxylic acid chloride with an acid hydrazide, and then the resulting carbothiohydrazide derivative containing an acyl group on the terminal N-atom is treated with acid to give the cyclic product.

In an analogous reaction benzodiazepines of formula (I) containing a [1,3,4]oxadiazole ring can be obtained, for example, if the above mentioned N-acyl-thiocarboxylic acid hydrazide derivative is treated with a sulfur binding reagent, for example mercury (II) acetate.

The 4,5-dihydro-2,3-benzodiazepin-3-carbothiohydrazides can serve as starting materials for further new compounds of formula (I) substituted with a hetero-ring. For example, if the N-methyl-carbamoyl-carbothiohydrazide obtained with methyl isocyanate is heated with concentrated acid, for example hydrochloric acid, then new compounds of formula (I) substituted with (5-oxo-4,5-dihydro-[1,3,4]thiadiazol-2-yl) group can be obtained. If the carbothiohydrazide derivative is reacted with bromoacetic acid ester, (5-oxo-5,6-dihydro-4H-[1,3,4]thiadiazin-2-yl)-[2,3]benzodiazepine derivatives having a 6-membered ring as the $R_3$ substituent are obtained. If the carbothiohydrazide derivatives are reacted with a α-halo-ketones, for example chioroacetone, then e.g., (5-methyl-6H-[1,3,4]thiadiazin-2-yl)-[2,3]benzodiazepines are formed.

The appropriate thiohydroxamic acids can be obtained from [2,3]benzodiazepin-3-thiocarboxylic acid chlorides with hydroxylamine, which can be transformed into heterocyclic compounds by reacting with bifunctional alkylating agents. Among others, [1,4,2]oxathiazol-3-yl-2,3-benzodiazepines can be synthesized for example from thiohydroxamic acid derivatives with methylene iodide.

The compounds of formula (I) containing 3-oxo-2,3-dihydro-[1,2,4]thiadiazol-5-yl group as $R^3$ substituent can be prepared, for example, by reacting the unsubstituted compounds of formula (II) with phenoxycarbonyl isothiocyanate, then the resulting phenoxycarbonyl-thiocarbamoyl-benzodiazepine transformed into N-alkyl-carbamoyl-thiocarbamoyl-benzodiazepine with primary amines and the latter is reacted e.g., with bromine to accomplish the ring closure between the sulfur and the nitrogen atoms.

The compounds of formula (I) containing 4,5-dihydro-oxazol-2-yl group as an $R^3$ substituent can be synthesized by reacting the compounds of formula (II) with chloroethyl isocyanate to give an urea derivative, which is heated in the presence of sodium iodide and potassium carbonate in dimethylformamide to accomplish the ring closure.

The compounds of formula (I) containing 2-alkyl-thiazol-4-yl group as $R^3$ substituent can be synthesized by reacting 3-bromo-acetyl-[2,3]benzodiazepines with the appropriate carboxylic acid thioamide.

From 3-cyano-2,3-benzodiazepines—obtained from 2,3-benzodiazepines of formula (II) with cyanogen bromide-2,3-benzodiazepines containing among others (1H-tetrazol-5-yl) as well as (5-alkyl-[1,2,4]oxadiazol-3-yl) groups as an $R^3$ substituent can be synthesized. The tetrazolyl compounds can be synthesized by reacting the nitrile derivative with sodium azide in dimethylformamide in the presence of ammonium chloride, while if the nitrile compound is first treated with hydroxylamine and the thus-obtained amidoxime is reacted with a carboxylic acid anhydride or chloride, then the appropriate 1,2,4-oxadiazolyl compounds can be obtained.

The compounds of formula (I) containing 1,2,4-triazolyl group as $R^3$ substituent can be synthesized from a 3-thiocarbamoyl-[2,3]benzodiazepine derivative by reacting first with methyl iodide, then the obtained S-methyl compound is condensed with hydrazine and the so formed intermediate is treated with a carboxylic acid anhydride or chloride.

Other illustrative processes for the synthesis of compounds of formula (I) are those, where a hemiketal of formula (IV) is reacted with a heterocyclic reagent substituted with a hydrazine group in the presence of an acid as catalyst. The condensation reaction can be carried out in the presence of hydrochloric acid as catalyst by heating e.g., in isopropanol or toluene and possibly with a Dean-Stark apparatus. It can be advantageous in some instances to first transform the hemiketal into an isochromenilium salt of formula (IVa) with a mineral acid e.g., perchloric acid and the latter is reacted with a hydrazine reagent, for example in isopropanol. The thus-obtained hydrazones of formula (VII) are generally formed as a mixture of stereoisomers. They can be further reacted e.g., with methanesulfonyl chloride in dichloromethane in the presence of triethylamine, and the mesylate obtained after isolation is treated with a concentrated solution of a base in an alcohol or a mixture of alcohol-dichloromethane. The ring closure reaction can be achieved for example, by the Mitsunobu reaction (Mitsunobu *Synthesis* 1:1 (1981)) as well.

If desired, the compounds of formula (I) obtained by different methods can be transformed into other compounds of formula (I) with further reactions. For example, a reactive halogen atom in the side chain of the heterocycle—the $R^3$ substituent—can be exchanged for an amino group, for example by heating with an excess of a proper amine, or the NH group of a N-containing heterocyclic compound can be alkylated by known methods. The latter transformation for example in the case of a triazolyl compound, can be carried out with methyl iodide in the presence of potassium tert-butoxide.

The reduction of the nitro group in the compounds of formula (I) is generally carried out in polar solvents at room temperature or at elevated temperature in the presence of catalysts such as Raney-nickel, platinum or palladium. Besides gaseous hydrogen, other hydrogen sources e.g., hydrazine hydrate, ammonium formate, potassium formate or cyclohexene can also be applied. The nitro group can be reduced, for example, with tin in the presence of an acid, or with tin (II) chloride by heating in an alcohol as well. The amino group can be further derivatised by known methods, for example alloation, acylation, or Sandmeyer reaction.

The AMPA antagonistic activity of the compounds of formula (I) of the present invention is exemplified by the following experiments. Reference to compounds by number refers to compounds described in the numbered examples below.

Inhibition of the AMPA Receptors

Two experimental models were used for the demonstration of the inhibition of the AMPA receptor activation of the compounds of formula (I). In the first model the spreading depression caused by glutamate agonists (i.e., AMPA or kainate) was studied, while in the second one the transmembrane ion-current induced by the activation of the AMPA/kainate receptors was measured directly.

Inhibition of AMPA Induced "Spreading Depression" in Isolated Chicken Retina The AMPA antagonistic effect of the compounds of formula (I) was studied in the in vitro "spreading depression" model (Sheardown *Brain Res.* 607:189 (1993)). The AMPA antagonists prolong the latency of the development of the "spreading depression" caused by AMPA (5 $\mu$M).

TABLE 1

Inhibition of the "spreading depression" in chicken retina
Compound (Number of example)/$IC_{50}$ $\mu$M

| GYKI 52466 (reference) | GYKI 53773 (reference) | 61 | 69 | 86 | 84 |
|---|---|---|---|---|---|
| 9.5 | 1.2 | 1–5 | 0.9 | 0.42 | 0.85 |

The data of Table 1 indicate that the compounds of the present invention inhibit the AMPA-induced "spreading depression" with an $IC_{50}$ value of 0.4–5 $\mu$M.

Inibition of AMPA Induced Transmembrane Currents

The activity of the compounds of the present invention was studied on acutely isolated cerebellar Purkinje cells by measuring the whole-cell current induced by 5 $\mu$M AMPA according for example to the method described by Bleakman et al. (*Neuropharmacology* 12:1689 (1996)). According to the $IC_{50}$ values obtained, the compounds of the present invention inhibit the AMPA-induced ion-current by one to two magnitudes greater than the internationally accepted reference compound GYKI 52466 (5-(4-aminophenyl)-9H-1,3-dioxolo[4,5-h][2,3]benzodiazepine, Hungarian patent No. 191 698), or GYKI 53773 ((R)-7-acetyl-5-(4-aminophenyl)-8,9-dihydro-8-methyl-7H-1,3-dioxolo[4,5-h][2,3]benzodiazepine, U.S. Pat. No. 5,536,832), the $IC_{50}$ values of which are 8.8 $\mu$M, and 1.57 $\mu$M, respectively. (See Table 2).

TABLE 2

Inhibition of the ion-currents caused by 5 $\mu$M AMPA determined by the whole cell patch clamp method
Compound (Number of example)/$IC_{50}$ $\mu$M

| GYKI 52466 (reference) | GYKI 53773 (reference) | 61 | 69 | 86 | 84 |
|---|---|---|---|---|---|
| 8.8 | 1.57 | 0.49 | 0.42 | 0.06 | 0.09 |

Anticonvulsant Activity

Although various drugs with different spectra of activity are used in the therapy of epilepsy, they show severe side effects. Furthermore, about 30% of epilepsy patients are refractory to these drugs. Consequently, there is a need for such new antiepileptic drugs, which act via a mechanism different from those in current use. There are great expectations towards those compounds that display their activity by diminishing the glutamate-induced over-activation of the central nervous system (*TIPS*, 15:456 (1994)).

The anti-seizure activity of some of the compounds of the present invention was measured using the electroshock test (*J. Pharmacol. Exp. Ther.* 106:319 (1952)) and the results are shown in Table 3. The spasmolytic activity of the compounds of the present invention was investigated by using e.g., pentetrazole (*J. Pharmacol. Exp. Ther.* 108:168 (1953)), strychnine (*J. Pharmacol. Exp. Ther.* 129:75 (1960)), bemegrid, nicotine, bicuculine, 4-aminopyridine and mercapto-propionic acid for inducing the clonic-tonic seizures and lethality. The investigated compounds were administered orally in three doses using 10 male CD1 mice/dose, usually 60 min before the induction of seizures. Non-limiting, illustrative results are summarized in Table 3.

TABLE 3

Investigation of the anticonvulsive activity in mice

Compound (Number of example)/$ED_{50}$ mg/kg po.

| Method | GYKI 52466 | GYKI 53773 | 61 | 69 | 86 | 84 | 89 | 102 |
|---|---|---|---|---|---|---|---|---|
| MES | 37.4 | 8.6 | 13.1 | 14.7 | 6.1 | 12.5 | 10.5 | 13.9 |
| MES 30' | 21.9 | 4.9 | 11.5 | 8.7 | 4.3 | 10–15 | — | — |
| Pentetrazol | 119.8 | 16.8 | 32.5 | 46.9 | 10.0 | 17.1 | 11.5 | 35.7 |
| Strychnine | 86.7 | 17.4 | 35.4 | 27.7 | 10.6 | 18.2 | 15.7 | 26.7 |
| Bemegride | 71.9 | 23.9 | 34.4 | 33.3 | 11.2 | 16.7 | 11.2 | 27.9 |
| Bicuculline | 35.0 | 14.6 | 31.0 | 18.1 | 4.6 | 17.0 | 17.1 | 25.8 |
| Nicotine | 71.8 | 22.7 | 59.3 | 16.8 | 16.5 | 77.2 | 45.9 | 31.7 |

TABLE 3-continued

Investigation of the anticonvulsive activity in mice

Compound (Number of example)/ED$_{50}$ mg/kg po.

| Method | GYKI 52466 | GYKI 53773 | 61 | 69 | 86 | 84 | 89 | 102 |
|---|---|---|---|---|---|---|---|---|
| 4-AP | 43.0 | 8.4 | 17.6 | 16.6 | 10.1 | 16.6 | 14.3 | 20.4 |
| 3-MPA | 47.0 | 17.1 | 11.0 | 34.2 | 4.0 | 6.8 | >50 | >50 |

Abbreviations:
MES = maximal electroshock seizure;
4-AP = 4-aminopyridine;
3-MPA = 3-mercapto-propionic acid The data provided above indicate that the compounds of formula (I) of the present invention showed significant anticonvulsive activity in all of the eight tests studied. They reveal both a broader spectrum and more significant anticonvulsive efficacy compared to GYKI 52466 and GYKI 53773, both used as reference compounds in the literature. The protective effect displayed against the different convulsion inducing agents predicts favorably for their potential use in the treatment of the different kinds of epilepsy.

Musde Relaxant Activity

Central muscle relaxants are used in such clinical situations when the resting tone of the skeletal muscles is increased as a consequence of a cerebral trauma or due to a chronic neurodegenerative illness, resulting in muscle rigidity or tremor. The muscle spasm is often painful and hinders normal motion.

The muscle relaxant activity of the compounds of formula (I) of the present invention was determined in the inclined screen test described by Randall (J. Pharmacol. Exp. Ther. 129:163 (1960)) as in the rotarod test (Dunham et al., J. Am. Pharm. Assoc. 46:208 (1957)). The compounds were administered in three doses intraperitoneally using 10 CD1-mice/dose. The muscle relaxant activity of the compounds of the present invention was compared to that of the reference compounds GYKI 52466 and GYKI 53773. Representative, non-limiting results are summarized in Table 4. From these data, it is evident, that the muscle relaxant activity of the compounds of the present invention significantly exceeds that of GYKI 53773, which is now in clinical phase-II studies.

TABLE 4

Muscle relaxant activity in mice

| Compound (Number of example) | Inclined screen ED$_{50}$ ip. (mg/kg) | Rotarod ED$_{50}$ ip. (mg/kg) |
|---|---|---|
| GYKI 52466 (reference) | 47.1 | 25.1 |
| GYKI 53773 (reference) | 13.4 | 2.3 |
| 61 | 10.7 | 5.4 |
| 69 | 12.2 | 1.2 |
| 86 | 3.9 | 0.8 |
| 84 | 12.8 | 1.4 |
| 89 | 4.3 | 1.7 |
| 102 | 14.8 | 2.9 |

The muscle relaxant activity of the compounds of formula (I) determined in the above tests indicates potential therapeutic use in the treatment of such illnesses in which the increased muscle tone causes problems. Considering their skeletal muscle relaxant and anti-tremor activity (discussed below), the compounds may be useful in the treatment of essential tremor, multiple sclerosis (spasms+tremor) and Parkinson's disease (rigidity+tremor).

The Inhibition of Focal Isohemia

The focal anti-ischemic activity of the compounds of formula (I) of the present invention was measured by the "middle cerebral artery occlusion" (MCAO) test (Bartus et al. Stroke Vol. 25, No. 11, 2265 (1994) and Sydserff et al., Brit. J. Pharmacol. 114:1631 (1995)). The blood supply of the left middle cerebral artery of anaesthetized rats was temporarily blocked (60 min) by an embolus introduced intra-arterially following Halothane anesthesia, without craniotomy, thereafter the perfusion was reestablished by removing the embolus and thus a human "stroke-like" status was triggered in an experimental animal mode. After a histological process (TTC staining) 24 h later, the infarcted area was dete mined by a computer assisted scanner program and was compared to the results obtained in a control group treated with the vehicle. Non-limiting, representative result are summarized in Table 5.

TABLE 5

Inhibition of focal ischemia in rats

| Compound (Number of example) | Dose mg/kg iv. (6× in every 30 min) | Decrease of the infracted area in % compared to that of the control | | |
|---|---|---|---|---|
| | | 30 min | 120 min | 180 min |
| | | Time of first treatment after occlusion | | |
| GYKI 52466 HCl (reference) | 2 | | 39* | |
| | 5 | 34* | 47** | |
| GYKI 53773 (reference) | 2 | 47* | 49** | 26 |
| 61 | 1 | | 63** | 16 |
| | 2 | | | 46* |
| 69 | 2 | | | 28 |
| 86 | 1 | | | 35* |

*p < 0.05;
**p < 0.01; calculated with Dunnett test following ANOVA (Dunnett J. Amer. Statist. Ass. 50: 1096 (1955))

The investigated compounds possess a strong neuroprotective activity in this experimental model, which is considered the model of the human stroke. Some of the compounds, e.g., those described in Example 61 and 86, show significant activity even when administered 3 h after the occlusion predicting a potential useful clinical application.

Inhibition of Autoimmune Inflammation

Multiple sclerosis is a chronic autoimmune inflammation of the central nervous system in which the axonal myelin coat, assuring the safe impulse conduction, is damaged. The aligodendrocytes forming the myelin coat express mainly AMPA/kainate receptors. Thus, the neurodegenerative process is further enhanced by glutamate, the excitatory neurotransmitter, which is released by the activated immune cells in large quantities which expresses its activity through AMPA/kainate receptors thereby damaging myalin oligodendrocytes and axons of neurons (Steinman *Nature Medicine* 6:15 (2000) and Werner et al., *J. Neurol. Transmiss. Suppl.*, 60:375 (2000)). As a consequence of these processes, at first mild neurological symptoms, such as visual, sensory, balance, motion an urogenital problems develop which become increasingly serious. The therapy of multiple sclerosis is still an unsolved problem despite the intense research being ursued in this field (Bjartmar et al., *Drugs of Today* 2002, 38(1), 17–29 (2002)).

Muscle spasticity and intention tremor belong to the most severe neurological symptoms of multiple sclerosis (Baker et al., *Nature* 404:84 (2000)). Moderation or cure of these symptoms by a proper therapy would be very important.

The activity of the 2,3-benzodiazepine derivatives possessing AMPA antagonistic activity was further investigated in an autoiunmune encephalomyelitis model (Smith et al., *Nature Medicine*, 6:62 (2000)) in rats, using immunization with guinea pig myelin basic protein (MBP) and complete Freund adjuvant. The compounds were administered intraperitoneally twice a day for 8 days, starting on day 10 after immunization and with an observation period until symptoms were present. 5–15 animals were used in each group. Their weights were 160–180 g (Lewis rats, female) and 180–220 g (Lewis rats, male). The activity of the compounds was determined according to the symptom score values, and compared to those of the control group (see Table 6). Histopathological investigations were carried out on the brain stem, the spinal cord, and the sciatic nerve (Gijbels et al., *J. Clin. Invest.* 94:2177 (1994)) using 5–10 animals/group. Non-limiting, representative results are presented in Table 7.

TABLE 6

Effect of 2,3-benzodiazepines possessing AMPA antagonist activity on the clinical symptoms of autoimmune encephalomyelitis in Lewis rats

| Compound (Number of example) | Dose (mg/kg ip.) | Neurological symptoms (change compared to controls, %) | | | |
|---|---|---|---|---|---|
| | | Female rats | | Male rats | |
| | | 0–8 day | 0–14 day | 0–8 day | 0–14 day |
| GYKI 53773 (reference) | 30 | −38* | −27 | −43* | −29 |
| | 15 | −60* | −63** | −8 | +7 |
| GYKI 52466 (reference) | 30 | −45 | −4 | −1 | −1 |
| 86 | 15 | −97** | −85** | −93* | −67 |
| | 7.5 | −62** | −66** | −65** | −70** |
| | 3.75 | −3 | −18 | −70** | −77** |
| | 1.875 | −40* | −39* | +5 | −8 |
| 61 | 7.5 | −56* | −53* | −60* | −63* |
| | 3.75 | −44 | −48 | −44* | −46* |
| | 1.875 | −18 | −7 | +13 | +5 |

TABLE 6-continued

Effect of 2,3-benzodiazepines possessing AMPA antagonist activity on the clinical symptoms of autoimmune encephalomyelitis in Lewis rats

| Compound (Number of example) | Dose (mg/kg ip.) | Neurological symptoms (change compared to controls, %) | | | |
|---|---|---|---|---|---|
| | | Female rats | | Male rats | |
| | | 0–8 day | 0–14 day | 0–8 day | 0–14 day |
| 69 | 7.5 | −29 | −24 | −51* | −50* |
| | 3.75 | +43 | +58* | +35 | −40* |

*$p < 0.05$;
**$p < 0.01$ (Mann-Whitney test)

TABLE 7

Effect of 2,3-benzodiazepine derivatives possessing AMPA antagonistic character on the histological and clinical symptoms of autoimmune encephalomyelitis in Lewis rats on day 24 after immunization.

| Compound (Number of example) | Dose (mg/kg ip.) | Histological symptoms (change, %) rats | | Neurological symptoms (change, %) rats | |
|---|---|---|---|---|---|
| | | Male | female | male | female |
| GYKI 53773 (reference) | 30 | +34 | −16 | −26 | −41 |
| 86 | 15 | −66 | −53 | −67 | −85 |
| | 7.5 | +1 | −22 | −66 | −62 |
| | 3.75 | +4 | −20 | −72 | −21 |
| | 1.875 | −25 | −15 | +54 | −42 |
| 61 | 7.5 | −20 | −5 | −54 | −53 |

According to our histopathological and pharmacological investigations the compounds described in, for example, Example 86 and 61 proved to be more active than the reference compound GYKI 53773.

The anti-tremor effect of the 2,3-benzodiazepine derivatives of the present invention, possessing AMPA antagonistic character in mouse models was studied using three tremorigen agents of different mechanism of action, such as oxotremorine (Rathbun et al., *Psychopharmacology*, 4:114 (1963)), GYKI 20039 (3-(2,6-dichlorophenyl)-2-iminothiazolidine; (Andrási et al., *Acta Physiol. Acad. Sci. Hung.* 37:183 (1970)) and harmaline. Number of animals: 5/group. Weight of animals: 20–25 g (CD1 mice, male). The activity of the investigated compounds was determined by their score values compared to those of the control group. The $ED_{50}$ values were calculated according to the Litchfield-Wilcoxon method and are listed in Table 8.

TABLE 8

Effect of 2,3-benzodiazepine derivatives possessing AMPA antagonistic character on the tremor of CD1 mice induced by different chemical agents.

| Compound (Number of example) | Dose range (mg/kg p.o.) | ED$_{50}$ (mg/kg po.) | | |
|---|---|---|---|---|
| | | Oxotremorin 1 mg/kg ip. | GYKI 20039 10 mg/kg ip. | Harmaline 40 mg/kg ip. |
| GYKI 52466 (reference) | 6.25–75.0 | 20.5(14.9–28.3) | 37.1(25.2–54.7) | 38.5(25.7–57.9) |
| GYKI 53773 (reference) | 3.125–20.0 | 5.6(3.6–8.5) | 10.6(7.2–15.5) | 9.0(−7.4–10.9) |
| 86 | 3.125–9.0 | 4.3(3.5–5.4) | 6.8(5.5–8.5) | 6.0(4.9–7.4) |

According to our investigations, the compound described in Example 86 was more active than the reference compounds GYKI 53773 and GYKI 52466, respectively.

The 2,3-benzodiazepine derivatives with AMPA antagonistic character, compensating for the harmful effect of glutamate by blocking the corresponding receptors, are therapeutically important. Their combined neuroprotective, muscle relaxant, tremor inhibiting etc. properties beneficially influence the progression of the pathological neurological disorders and diminish the pathological neurological symptoms, respectively.

The Effect of the Compounds of the Present Invention on the Acute and Chronic Inflammatory Disorders of the Airways Bronchial hyperresponsiveness (BHR) and airway eosinophilia (AEP) are characteristic features of bronchial asthma. BHR is typified by an exaggerated response to a wide variety of stimuli that can induce an increased resistance to airflow in the airways. AEP is a result of prolonged eosmophil infiltration, mast cell, and T cell activation in the airways. In actively (e.g., ovalbumin) immunized rats (e.g., Brown Norway [BN] strain), repeated sensitization followed by antigenic challenge results in lung eosinophilia and bronchial hyperresponsiveness to different spasmogens (e.g., acetylcholine). This is the most frequently employed model for studying potential anti-asthmatic effects of new chemical entities.

BN rats were actively immunized with allergen (ovalbumin). On day one rats were sensitized with the subcutaneous administration of ovalbumin suspended in Al(OH)$_3$ (2.5 μg ovalbumin+20 mg Al(OH)$_3$ in 0.5 ml saline). Booster injections (same dose and same route) were given at day 14 and 21. Simultaneously at each occasion 0.25 ml of Bordatella pertussis vaccine was injected intraperitoneally. On day 28, animals were challenged by inhalation of the antigen (vaporized 1% OVA solution for 1 hour). Test compounds were administered orally 2 hours pre-challenge.

48 hours following challenge, they were sacrificed by an overdose of urethane (4–5 ml of 15% urethane given i.p.), bronchoalveolar lavage fluid (BALF) was obtained, and tracheae dissected from the animals. Eosinophil cell count (cells/ml BALF) was determined manually using a selective stain for eosinophils and counting the cells in a Buerker chamber. BHR was determined using tracheal rings suspended in an organ bath. After an equilibration period of 30 minutes, cumulative concentration response curves to acetyicholine were determined. Maximal response of control (unchallenged, non-treated) tracheal rings is obtained at 10$^{-3}$ M acetyicholine. The height of this response is defined as 100%. All other contractions are expressed as a percentage and related to the control response.

Results

TABLE 9

Effect of GYKI 52466 (reference), GYKI 53773 (reference) and the compound described in Example 86 on the bronchial hypersensitivity and the eosinophilia of the airways on BN-rats sensitized with ovalbumin and antigen challenged by inhalation (mean ± SE, p determined by Student's t-test).

| Experiment | Parameter | Control | Challenge | Compound (Number of example) GYKI 52466 (reference) 3.0 mg/kg po |
|---|---|---|---|---|
| 1 | ED$_{50}$* | 5.63 ± 0.46 | 6.74 ± 1.45 | 5.60 ± 1.53 |
| | p | 0.002 | | 0.028 |
| | MAX** | 100 ± 0 | 276 ± 217 | 135 ± 105 |
| | p | 0.001 | | 0.037 |
| | Eosinophil*** | 0.17 ± 0.01 | 1.24 ± 0.23 | 0.91 ± 0.13 |
| | p | 0.010 | | NS‡ |

| Experiment | Parameter | Control | Challenge | GYKI 53773 (reference) 3.0 mg/kg po |
|---|---|---|---|---|
| 2 | ED$_{50}$* | 5.22 ± 0.59 | 5.89 ± 0.66 | 4.64 ± 0.91 |
| | p | 0.003 | | 0.001 |
| | MAX** | 100 ± 0 | 163 ± 65 | 85 ± 43 |
| | p | <0.001 | | 0.007 |
| | Eosinophil*** | 0.38 ± 0.11 | 1.24 ± 0.13 | 1.29 ± 0.11 |
| | p | 0.004 | | NS‡ |

| Experiment | Parameter | Control | Challenge | 86 3.0 mg/kg po |
|---|---|---|---|---|
| 3 | ED$_{50}$* | 5.78 ± 0.17 | 6.99 ± 0.32 | 4.95 ± 0.59 |
| | p | 0.001 | | 0.008 |
| | MAX** | 100 ± 0 | 255 ± 50 | 81 ± 14 |
| | p | 0.001 | | 0.003 |
| | Eosinophil*** | 0.23 ± 0.08 | 1.43 ± 0.27 | 1.32 ± 0.32 |
| | p | 0.005 | | NS‡ |

*acetylcholine (Ach) concentration (-log M) which causes a 50% contraction compared to the control
**relative contraction compared to the control at a maximal Ach concentration
***BALF eosinophil number (×10$^6$/ml)
‡not significant (p > 0.05)

The representative results presented in Table 9 show that representative compounds according to the present invention diminished the bronchial hyperresponsiveness caused by the allergen. The eosinophulia was not significantly influenced by the applied doses.

The results of the different pharmacological investigations mentioned above show that the compounds of formula (I) of this invention are able to beneficially influence various diseases and disorders in which glutamate (AMPA/kainate) receptors have been implicated. Consequently the compounds according to the invention are suitable for treating neurological and psychiatric disorders, triggered by the extremely enhanced activity of the AMPA receptor. Therefore, they have therapeutic utility as anticonvulsants, muscle relaxants, as well as neuroprotective agents. They also display therapeutic value for the treatment of epilepsy, as well as different illnesses in which the spasm of skeletal-muscles is involved, and in the treatment of neurodegenerative disorders such as e.g., cerebral ischemia (stroke).

Exemplary neurological illnesses which can be beneficially influenced or prevented include Parkinson's disease, Alzheimer's disease, Huntington chorea, amyotrophic lateral sclerosis, olivopontocerebellaric atrophy, AIDS dementia, senile dementia. A similar beneficial effect can be achieved in the treatment of neurodegenerative processes caused by cerebrovascular catastrophe (stroke, brain, and spinal injuries) or hypoxia, anoxia or hypoglycemia. The compounds of the invention can be advantageously used for the treatment of different psychiatric diseases such as anxiety, schizophrenia, sleep disorders, as well as alleviating the withdrawal syndrome of alcohol and drug abuse. Furthermore they may inhibit tolerance development in the case of sedatives or analgesics.

It can be expected that they can be advantageously used in epileptic disease entities, in the cure or palliation of muscle spasms of central origin and in the relief of pathologic pain as well as in the treatment of urinary incontinence.

In one aspect of the invention, a method of blocking the activation of one or more excitatory amino acid receptors in mammals is provided. This method includes administering to a mammal in need of such treatment a pharmaceutically effective amount of a compound of the formula (I).

In another aspect of the invention, a method of treating epilepsy in mammals is provided. This method includes administering to a mammal in need of such treatment an antiepileptic amount of a compound of the formula (I).

In another aspect of the invention, a method of treating spasms of the skeletal musculature in mammals is provided. This method includes administering to a mammal in need of such treatment a muscle-relaxing amount of a compound of the formula (I).

In still another aspect of the invention, a method of treating acute and chronic neurodegenerative disorders in mammals is provided. This method includes administering to a mammal in need of such treatment a pharmaceutically effective amount of a compound of the formula (I).

In yet another aspect of the invention, a method for treating inflammatory disorders in mammals is provided. This method includes administering to a mammal in need of such treatment a pharmaceutically effective amount of a compound of the formula (I).

In other aspects of the invention, the compounds of formula (I) can be advantageously used in the treatment of multiple sclerosis. A further therapeutic field, in which the compounds of formula (I) can be used, are illnesses that are caused by the over-function of the periferic glutamate receptors. Such illnesses include the acute and chronic inflammatory disorders of the airways particularly allergic inflammations such as asthma-related pathologies. This latter potential therapeutic use is supported by the results obtained in ovalbumin sensitized rats.

In one aspect of the invention, a pharmaceutical composition is provided including a compound of formula (I), or a stereoisomer, or a pharmaceutically acceptable salt thereof and a pharmaceutically acceptable carrier, excipient or diluent.

The compounds of formula (I) are formulated in a pharmaceutically acceptable vehicle with any of the well-known pharmaceutically acceptable carriers, including diluents and excipients (see *Remington's Pharmaceutical Sciences,* 18th Ed., Gennaro, Mack Publishing Co., Easton, Pa. 1990 and *Remington: The Science and Practice of Pharmacy,* Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of pharmaceutical compositions may contain more than one type of compound of formula (I), as well as any other pharmacologically active ingredient useful for the treatment of the particular conditions, disease, or symptom being treated.

The compositions of the invention can be administered by standard routes (e.g., oral, inhalation, rectal, nasal, topical, including buccal and sublingual, or parenteral, including subcutaneous, intramuscular, intravenous, intradermal, transdermal, and intratracheal). In addition, polymers may be added according to standard methodologies in the art for sustained release of a given compound.

For oral administration, the compositions of the invention may be presented as discrete units such as capsules, caplets, gelcaps, cachets, pills, or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc. Alternately, administration of a composition including the compound of formula (I) may be effected by liquid solutions, suspensions or elixirs, powders, lozenges, micronized particles and osmotic delivery systems.

Formulations suitable for administration by inhalation include formulations that can be dispensed by inhalation devices known to those in the art. Such formulations may include carriers such as powder and aerosols. Liquid and powdered compositions suitable for nebulization and intrabronchial use, or aerosol compositions administered via an aerosol unit dispensing metered doses ("MDI") are contemplated.

The active ingredient maybe formulated in an aqueous pharmaceutically acceptable inhalant vehicle, such as, for example, isotonic saline or bacterostatic water and other types of vehicles that are well known in the art. The solutions are administered by means of a pump or squeeze-actuated nebulized spray dispenser, or by any other conventional means for causing or enabling the requisite dosage amount of the liquid composition to be inhaled into the patient's lungs.

Powder compositions include, by way of illustration, pharmaceutically acceptable powdered preparations of the active ingredient thoroughly intermixed with lactose or other inert powders acceptable for intrabronchial administration. The powder compositions can be administered via a dispenser, including, but not limited to, an aerosol dispenser or encased in a breakable capsule, which may be inserted by the patient into a device that punctures the capsule and blows the powder out in a steady stream.

Aerosol formulations for use in the subject method typically include propellants, surfactants, and co-solvents and may be filled into conventional aerosol containers that are closed by a suitable metering valve.

Formulations suitable for nasal administration, wherein the carrier is a solid, include a coarse powder having a particle size, for example, in the range of 20 to 500 microns which is administered in the manner in which snuff is administered, i.e. by rapid inhalation through the nasal passage from a container of the powder held close up to the nose. Suitable formulations, wherein the carrier is a liquid, for administration, for example via a nasal spray, aerosol, or as nasal drops, include aqueous or oily solutions of the compound of formula (I).

Formulations suitable for parenteral administration include aqueous and non-aqueous sterile injection solutions which may contain antioxidants, stabilizers, buffers, bacteriostats and solutes which render the formulation isotonic with the blood of the intended recipient; and aqueous and non-aqueous sterile suspensions which may include suspending agents and thickening agents.

The dosage of the active ingredient depends on the route of administration, the type and severity of the disease as well as the weight and age of the patient. The daily dose for adult patients can be 0.1–500 mg, preferably 1–100 mg, in a single dose or divided in several doses.

In another aspect of the present invention, a method is provided for treating (a) an acute or chronic neurodegenerative disease associated with glutamate dysfunction; (b) a method for treating epilepsy, (c) a method for reducing muscle spasm in mammals; (d) a method for preventing, treating or alleviating the symptoms of acute or chronic inflammatory disorders of the airways; (e) a method for relief of pathological pain in mammals. These methods include administering to a mammal in need of such treatment a therapeutically effective amount of a compound of formula (I).

The term "therapeutically effective amount" is used to denote treatments at dosages effective to achieve the therapeutic result sought. Furthermore, one of skill will appreciate that the therapeutically effective amount of the compound of the invention may be lowered or increased by fine-tuning and/or by administering more than one compound of the invention, or by administering a compound of the invention with another pharmacologically active compound. The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect.

It will be appreciated by those of skill in the art that the number of administrations of the compounds according to the invention will vary from patient to patient based on the particular medical status of that patient at any given time.

The compounds according to the invention and the process for their preparation are illustrated in detail by the following Examples.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

The starting materials of the examples were synthesized as follows:

(±)-8-Methyl-5-(4-nitrophenyl)-7-thiocarbamoyl-8,9-dihydro-7H-1,3-dioxolo[4,5-h][2,3]benzodiazepine (I)

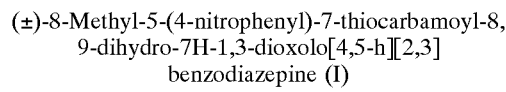

A mixture of 0.90 g (9.26 mmol) of potassium thiocyanate, 2.00 g (6.15 mmol) of (±)-8-methyl-5-(4-nitrophenyl)-8,9-dihydro-7H-1,3-dioxolo[4,5-h][2,3]benzodiazepine and 40 ml of acetic acid was stirred at 100–110° C. for 6 h. After cooling, the precipitated crystals were filtered off, washed with water and dried to yield 1.80 g (76%) of the title compound. Mp.: 242–243° C.

The thiocarbamoyl compounds II–X were synthesized from the corresponding dihydro-[2,3]benzodiazepine according to the above procedure.

(R)-8-Methyl-5-(4-nitrophenyl)-7-thiocarbamoyl-8,9-dihydro-7H-1,3-dioxolo[4,5-h][2,3]benzodiazepine (II)

Mp.: 213–215° C. Yield: 73%, $[\alpha]_D$: −251° (c=0.5; $CHCl_3$).

(S)-8-Methyl-5-(4-nitrophenyl)-7-thiocarbamoyl-8,9-dihydro-7H-1,3-dioxolo[4,5-h][2,3]benzodiazepine (III)

Mp.: 213–214° C. Yield: 76%, $[\alpha]_D$: +252° (c=1; $CHCl_3$).

(±)-8-Methyl-5-(3-methyl-4-nitrophenyl)-7-thiocarbamoyl-8,9-dihydro-7H-1,3-dioxolo[4,5-h][2,3]benzodiazepine (IV)

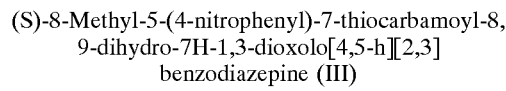

Mp.: 230–236° C. Yield: 86%.

(±)-8-Chloro-4-methyl-(4-nitrophenyl)-3-thiocarbamoyl-4,5-dihydro-3H-[2.3]benzodiazepine (V)

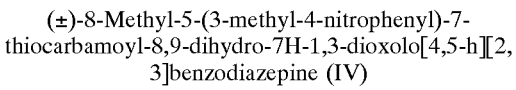

Mp.: 261–265° C. Yield: 72%.

(±)-7,8-Dichloro-4-methyl-1-(4-nitrophenyl)-3-thiocarbamoyl-4,5-dihydro-3H-[2,3]benzodiazepine (VI)

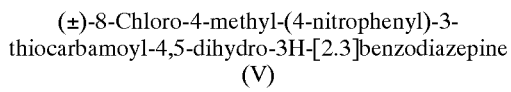

Mp.: amorphous. Yield: 59%.

(±)-8-Methyl-5-phenyl-7-thiocarbamoyl-8,9-dihydro-7H-1,3-dioxolo[4,5-h][2,3]benzodiazepin (VII)

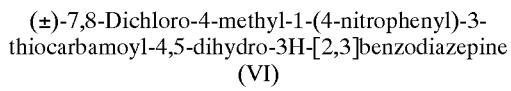

Mp.: 225–235° C. Yield: 86%.

5-(4-Nitrophenyl-7-thiocarbamoyl-8,9-dihydro-7H-1,3-dioxolo[4,5-h][2,3]benzodiazepine (VIII)

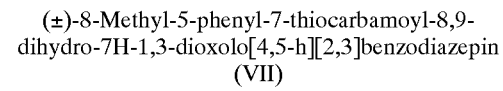

Mp.: 235–238° C. Yield: 62%.

(±)-8-Methyl-5-(4-methyl-3-nitrophenyl-7-thiocarbamoyl-8,9-dihydro-7H-1,3-dioxolo[4,5-h][2,3]benzodiazepine (IX)

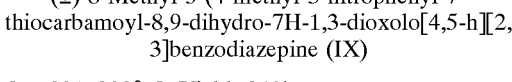

Mp.: 201–202° C. Yield: 84%.

(±)-7-Bromo-4-methyl-8-methoxy-1-(4-nitrophenyl)-3-thiocarbamoyl-3,4-dihydro-3H-[2,3]benzodiazepine (X)

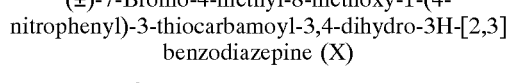

Mp.: 250–253° C. Yield: 94%.

(±)-8-Methyl-5-(4-nitrophenyl)-8,9-dihydro-7H-1,3-dioxolo[4,5-h][2,3]benzodiazepine-7-carbothioyl chloride (XI)

3.25 g (10.0 mmol) of (±)-8-methyl-8,9-dihydro-7H-1,3-dioxolo[4,5-h][2,3]benzodiazepine was dissolved in 90 ml of dry toluene by warming and after adding 2.17 ml (15.5 mmol) of triethylamine, was reacted with 1.90 ml (15.0 mmol) of trimethylsilyl chloride at about 28–30° C. After stirring at room temperature for 16 h this reaction mixture was added dropwise over a period of about 2 h to the solution of 1.38 g (12.0 mmol) of thiophosgene in 30 ml of dry toluene. This mixture was stirred at room temperature for 5 h, and then diluted with 30 ml of toluene. It was then decomposed by addition of 30 ml of water. After separation, the toluene phase was washed twice with 30 ml of water, followed by a 10% aqueous sodium chloride solution. After drying, the solvent was evaporated and the residue was treated with diisopropyl ether to yield 3.27 g (81%) of the crude product.

The crude product was recrystallized from chloroform, petroleum ether.

Yield: 3.05 g. Mp.: about 185° C. it rectystallizes, then it melts at 210° C.

The carbothioyl chloride type compounds XII–XVII were synthesized by analogous methods from racemic or optically active dihydro-[2,3]benzodiazepine derivatives:

(R)-8-Methyl-5-(4-nitrophenyl)-8,9-dihydro-7H-1,3-dioxolo[4,5-h][2,3]benzodiazepine-7-carbothioyl chloride (XII)

Mp.: 187–188° C. Yield: 80%, [α]$_D$: –610° (c=0.5; (CHCl$_3$).

(±)-8-Methyl-5-(3-nitrophenyl)-8,9-dihydro-7H-1,3-dioxolo[4,5-h][2,3]benzodiazepine-7-carbothioyl chloride (XIII)

Mp.: 198–199° C. Yield: 79%.

(±)-8-Methyl-5-(3-methyl-4-nitrophenyl)-8,9-dihydro-7H-1,3-dioxolo[4,5-h][2,3]benzodiazepine-7-carbothioyl chloride (XIV)

Mp.: 210–215° G. Yield: 79%.

(±)-8-Methyl-5-(4-methyl-3-nitrophenyl)-8,9-dihydro-7H-1,3-dioxolo[4,5-h][2,3]benzodiazepine-7-carbothioyl chloride (XV)

Mp.: 201–202° C. Yield: 84%.

(±)-8-Chloro-4-methyl-1-(4-nitrophenyl)-4,5-dihydro-3H-[2,3]benzodiazepine-3-carbothioyl chloride (XVI)

Mp.: 210–214° C. (DMF). Yield: 70%.

(±)-7-Bromo-4-methyl-8-methoxy-1-(4-nitrophenyl)-4,5-dihydro-3H-[2,3]benzodiazepine-3-carbothioyl chloride (XVII)

Mp.: 199–204° C. Yield: 82%.

(±)-8-Methyl-5-(4-nitrophenyl)-8,9-dihydro-7H-1,3-dioxolo[4,5-h][2,3]benzodiazepine-7-carbothiohydrazide (XVIII)

1.0 g (2.47 mmol) of carbothioyl chloride XI was added to a stirred solution of 0.37 g (7.42 mmol) of hydrazine hydrate in 15 ml of tetrahydrofuran at 5–10° C. over a period of about 0.5 h, then after 1 h stirring, the mixture was poured into water and the precipitated product was filtered off to yield 0.89 g (90%) of the crude product. After drying, it was used in the further reaction steps. The melting point of the product after recrystallization from ethanol was 196° C.

The carbothiohydrazide derivatives XIX–XXII were synthesized by analogous methods:

(R)-8-Methyl-5-(4-nitrophenyl)-8,9-dihydro-7H-1,3-dioxolo[4,5-h][2,3]benzodiazepine-7-carbothiohydrazide (XIX)

Mp.: 140–142° C. Yield: 99%, [α]$_D$: –201° (c=0.5; CHCl$_3$).

(±)-8-Chloro-4-methyl-1-(4-nitrophenyl)-4,5-dihydro-3H-[2,3]benzodiazepine-3-carbothiohydrazide (XX)

Mp.: 210–211° C. Yield: 61%.

(±)-7-Bromo-4-methyl-8-methoxy-1-(4-nitrophenyl)-4,5-dihydro-3H-[2,3]benzodiazepine-3-carbothiohydrazide (XXI)

Mp.: 196–201° C. Yield: 98%.

(±)-8-Methyl-5-(3-methyl-4-nitrophenyl)-8,9-dihydro-7H-1,3-dioxolo[4,5-h][2,3]benzodiazepine-7-carbothiohidrazide (XXII)

Mp.: 188–190° C. Yield: 98%.

(±)-8-Methyl-5-(4-nitrophenyl)-8,9-dihydro-7H-1,3-dioxolo[4,5-h][2,3]benzodiazepine-7-carbonitrile (XXIII)

A mixture of 3.25 g (10 mmol) of (±)-8-methyl-5-(4-nitrophenyl)-8,9-dihydro-7H-1,3-dioxolo[4,5-h][2,3]benzodiazepine, 20 ml of dimethylformamide, 2.76 g (20 mmol) of potassium chloride and 1.80 g (17 mmol) of cyanogen bromide was stirred at room temperature for 20 h. After pouring into water, the precipitated crystals were filtered off, and washed with water to yield 3.34 g (95%) of the title compound, Mp.: 172–176° C.

(±)-8-Methyl-5-(4-nitrophenyl)-8,9-dihydro-7H-1,3-dioxolo[4,5-h][2,3]benzodiazepine-7-carbamidoxime (XXIV)

A mixture of 2.80 g (8.0 mmol) of compound XXIII, 30 ml of 2-methoxyethanol, 0.84 g (10 mmol) of sodium acetate and 0.60 g (8.8 mmol) of hydroxylamine hydrochloride was stirred for 0.5 h, then concentrated in vacuum. The residue was treated with water, the precipitated crystals were filtered off and washed with water to yield 3.05 g (100%) of the title compound, Mp.: 138–145° C.

(±)-8-Methyl-5-(4-nitrophenyl)-8,9-dihydro-7H-1,3-dioxolo[4,5-h][2,3]benzodiazepine-7-carboxylic acid (2-chloroethyl)-amide (XXV)

A mixture of 1.0 g (3.07 mmol) of (±)-8-methyl-5-(4-nitrophenyl)-8,9-dihydro-7H-1,3-dioxolo[4,5-h][2,3]benzodiazepine, 25 ml of dry dichloromethane and 0.62 g (5.88 mmol of 2-chloroethyl isocyanate was stirred at room temperature for 24 h, then concentrated. The residue was purified by refluxing in ethanol to yield 1.25 g (94%) of the title compound, Mp.: 222–223° C.

(±)-Phenyl (8-methyl-5-(4-nitrophenyl)-8,9-dihydro-7H-1,3-dioxolo [4,5-h][2,3]benzodiazepine-3-carbothioyl)-carbamate (XXVI)

0.37 g (3.80 mmol) of potassium thiocyanate was dissolved in 8 ml of acetone, then 0.48 ml (3.80 mmol) of phenyl chloroformate was added dropwise to the mixture at room temperature. The reaction mixture was stirred at room temperature for 0.5 h, then at 40° C. for 0.25 h. Then the mixture was cooled with ice-water and a solution of 1.04 g (3.20 mmol) of (±)-8-methyl-5-(4-nitrophenyl)-8,9-dihydro-7H-1,3-dioxolo[4,5-h][2,3]benzodiazepine in 15 ml of acetone was added dropwise over a period of 0.5 h. After stirring for 0.5 h the bulk of the solvent was evaporated and the residue was treated with water, the crystals were filtered and washed with water to yield 1.73 g, (90%) of the title compound. Mp.: 160° C.

(±)-1-Methyl-3-{8-methyl-5-(4-nitrophenyl)-8,9-dihydro-7H-1,3-dioxolo[4,5-h][2,3]benzodiazepine-7-carbothioyl}-urea (XXVII)

1.57 g (3.11 mmol) of compound XXVI was dissolved in 8 ml of dimethylformamide and 0.35 ml (4.04 mmol) of 40% aqueous methylamine solution was added dropwise to the ice cooled stirred solution. After stirring for 2 h the mixture was poured into water, the precipitated crystals were filtered off and washed with water to yield 1.56 g of the crude product, which was recrystallized from ethanol. Yield: 1.01 g (73%). Mp.: 192–193° C.

The compounds XXVIII and XXIX were synthesized analogously.

(±)-1-Cyclopropyl-3-{8-methyl-5-(4-nitrophenyl)-8,9-dihydro-7H-1,3-dioxolo[4,5h][2,3]benzodiazepine-7-carbothioyl}-urea (XXVIII)

Mp.: 281–283° C. (ethyl acetate). Yield: 80%.

(±)-1-Ethyl-3-{8-methyl-5-(4-nitrophenyl)-8,9-dihydro-7H-1,3-dioxolo[4,5-h][2,3]benzodiazepine-7-carbothioyl}-urea (XXIX)

Mp.: 176–177° C. (methanol). Yield: 73%.

(±)-1-{8-Methyl-5-(4-nitrophenyl)-8,9-dihydro-7H-1,3-dioxolo[4,5-h][2,3]benzodiazepine-7-carbothioyl}-4-methyl-semicarbazide (XXX)

To a stirred solution of 0.40 g (1.0 mmol) of compound XVIII in 15 ml of chloroform 0.07 ml (1.2 mmol) of methyl isocyanate was added. After 1 h the reaction mixture was washed with sodium hydrogen carbonate solution and water and after concentration the obtained solid material was purified by refluxing in ethanol. The desired product was 0.36 g, yield: 88%. Mp.: 200° C.

(R)-8-Methyl-5-(3-methyl-4-nitrophenyl)-8,9-dihydro-7H-1,3-dioxolo[4,5-h][2,3]benzodiazepine (XXXI)

The title compound was prepared on based on the procedures described in the literature (Ling et al., *J. Chem. Soc. Perkin Trans.* 1:1423 (1995)) and the British patent specification No. 2,311,779.

Mp.: 159–160° C. (ethanol). $[\alpha]_D$: +172° (c=1; CHCl$_3$).

(R)-7-(tert-Butoxycarbonyl)-8-methyl-5-(4-nitrophenyl)-8,9-dihydro-7H-1,3-dioxolo[4,5-h][2,3]benzodiazepine (XXXII)

The compound was prepared according to a synthesis described in literature (Anderson et al., *J. Am. Chem. Soc.* 117: 12358(1995)) with the exception that tert-butyl carbazate was used instead of acetic hydrazide.

Mp.: 168–169° C. (isopropanol). $[\alpha]_D$: −444° (c=0.6; CHCl$_3$).

Example 1

(±)-8-Metyl-5-(4-nitrophenyl)-7-(2-thiazolyl)-8,9-dihydro-7H-1,3-dioxolo[4,5-h][2,3]benzodiazepine A mixture of 1.00 g (2.60 mmol) of the starting material I, 2.54 g (12.89 mmol) of bromoacetaldehyde diethyl acetal and 10 ml of dimethylformamide was stirred at 80° C. for 40 min. Then the reaction mixture was diluted with water and the crude product obtained was recrystallized from ethanol to yield 0.85 g (80%) of the title compound. Mp.: 145–150° C.

Example 2

(R)-8-Methyl-5-(4-nitrophenyl)-7-(2-thiazolyl)-8,9-dihydro-7H-1,3-dioxolo[4,5-h][2,3]benzodiazepine The title compound was obtained from the starting material II according to the method described in Example 1. Mp.: 108–110° C., yield: 89%, $[\alpha]_D$: +514° (c=0.5; CHCl$_3$).

Example 3

(S)-8-Methyl-5-(4-nitrophenyl)-7-(2-thiazolyl)-8,9-dihydro-7H-1,3-dioxolo[4,5-h][2,3]benzodiazepine The title compound was obtained from the starting material III according to the method described in Example 1. Mp.: 114–116° C., yield: 83%, $[\alpha]_D$: −522° (c=0.6; CHCl$_3$).

Example 4

(±)-8-Methyl-7-(4-methyl-thiazol-2-yl)-5-(4-nitrophenyl)-8,9-dihydro-7H-1,3-dioxolo[4,5-h][2,3]benzodiazepine A mixture of 0.76 g (1.98 mmol) of the starting material I, 1.10 g (11.88 mmol) of chloroacetone and 15 ml of dimethylformamide was stirred at 80–90° C. for 40 min. Then the reaction mixture was diluted with water, the precipitated crystals were filtered off, dried and purified by refluxing in ethanol to yield 0.69 g (82%) of the title compound; Mp.: 188–189° C.

Example 5

(±)-8-Methyl-7-(5-methyl-thiazol-2-yl)-5-(4-nitrophenyl)-8,9-dihydro-7H-1,3-dioxolo[4,5-h][2,3]benzodiazepine A mixture of 1.50 g (3.90 mmol) of starting material I, 3.57 g (19.50 mmol) of 2-bromopropionaldehyde dimethyl acetal and 15 ml of dimethylformamide was stirred at 90° C. for 1.5 h. Then the reaction mixture was diluted with water and the crude product obtained was purified by column chromatography using silica gel (MN Kieselgel 60; Macherey-Nagel, Düren, Germany) as adsorbent and a mixture of toluene-ethyl acetate (16:1) as eluent to yield 1.08 g (66%) of the title compound; Mp.: 193–195° C.

Example 6

(±)-7-(4,5-Dimethyl-thiazol-2-yl)-8-methyl-5-(4-nitrophenyl)-8,9-dihydro-7H-1,3-dioxolo[4,5-h][2,3]benzodiazepine A mixture of 0.60 g (1.56 mmol) of the starting material I, 1.02 g (9.57 mmol) of 3-chloro-2-butanone and 8 ml of dimethylformamide was stirred at 90° C. for 3 h. After cooling the precipitated crystals were filtered off, dried and purified by recrystallization from dimethylformamide and water to yield 0.49 g (76%) of the title compound; Mp.: >260° C. (dec.).

Example 7

(±)-8-Methyl-5-(4-nitrophenyl)-7-(4-phenyl-thiazol-2-yl)-8,9-dihydro-7H-1,3-dioxolo[4,5-h][2,3]benzodiazepine A mixture of 0.45 g (1.17 mmol) of the starting material I, 0.35 g (1.76 mmol) of phenyl bromide and 7 ml of dimethylformamide was stirred at 80° C. for 30 min. After cooling the precipitated crystals were filtered off, washed with ethanol and dried to yield 0.50 g (88%) of the title compound; Mp.: >260° C. (dec.).

Example 8

(±)-7-(4-Ethoxycarbonyl-thiazol-2-yl)-8-methyl-5-(4-nitrophenyl)-8,9-dihydro-7H-1,3-dioxolo[4,5-h][2,3]benzodiazepine A mixture of 0.45 g (1.17 mmol) of the starting material I, 0.46 g (2.36 mmol) of ethyl bromopyruvate and 7 ml of dimethylformamide was stirred at 80° C. for 30 min. After cooling the precipitated crystals were filtered off, washed with ethanol and dried to yield 0.41 g (85%) of the title compound; Mp.: 242–243° C.

Example 9

(±)-7-(4,5-Dihydro-thiazol-2-yl)-8-methyl-5-(4-nitrophenyl)-8,9-dihydro-7H-1,3-dioxolo[4,5-h][2,3]benzodiazepine A mixture of 1.00 g (2.6 mmol) of the starting material I, 2.13 g (10.40 mmol) of 2-bromoethylarmine hydrobromide and 10 ml of dimethylformamide was stirred at 90–100° C. for 4 h. After diluting with water the precipitated crystals were filtered off, dissolved in dichloromethane and washed several times with 10% sodium hydrogen carbonate solution. After drying the product was purified by column chromatography using silica gel (MN Kieselgel 60) as adsorbent and a mixture of hexane-ethyl acetate (1:1) as eluent to yield 0.80 g (75%) of the title compound; Mp.: 185–187° C.

Example 10

(R)-7-(4,5-Dihydro-thiazol-2-yl)-8-methyl-5-(4-nitrophenyl)-8,9-dihydro-7H-1,3-dioxolo[4,5-h][2,3]benzodiazepine The title compound was obtained from the starting material II according to the method described in Example 9.
Mp.: 118–124° C. Yield: 73%, $[\alpha]_D$: +575° (c=0.4; $CHCl_3$).

Example 11

(S)-7-(4,5-Dihydro-thiazol-2-yl)-8-methyl-5-(4-nitrophenyl)-8,9-dihydro-7H-1,3-dioxolo[4,5-h][2,3]benzodiazepine The title compound was obtained from the starting material III according to the method described in Example 9.
Mp.: 120–125° C. Yield: 71%. $[\alpha]_D$: −594° (c=0.4; $CHCl_3$).

Example 12

(±)-7-(4,5-Dihydro-4-oxo-thiazol-2-yl)-8-methyl-5-(4-nitrophenyl)-8,9-dihydro-7H-1,3-dioxolo[4,5-h][2,3]benzodiazepine A mixture of 1.00 g (2.6 mmol) of the starting material I, 1.19 g (7.78 mmol) of methyl bromoacetate and 10 ml of dimethylformamide was stirred at 80–90° C. for 1 h. After diluting with water the obtained crude product was purified by refluxing in methanol to yield 1.00 g (91%) of the title compound; Mp.: 218–220° C.

Example 13

(±)-7-(4,5-Dihydro-5-methyl-4-oxo-thiazol-2-yl)-8-methyl-5-(4-nitrophenyl)-8,9-dihydro-7H-1,3-dioxolo[4,5-h][2,3]benzodiazepine A mixture of 1.00 g (2.60 mmol) of the starting material I, 0.94 g (5.19 mmol) of ethyl 2-bromopropionate and 10 ml of dimethylformamide was stirred at 80–90° C. for 2 h. After diluting with water the obtained crude product was purified by refluxing in 15 ml of ethanol to yield 1.08 g (95%) of the title compound; Mp.: 213–214° C.

Example 14

(±)-7-(5,6-Dihydro-4-oxo-4H-1,3-thiazin-2-yl)-8-methyl-5-(4-nitrophenyl)-8,9-dihydro-7H-1,3-dioxolo[4,5-h][2,3]benzodiazepine A mixture of 2.00 g (5.20 mmol) of the starting material I, 1.89 g (10.44 mmol) of ethyl 3-bromopropionate and 20 ml of dimethylformamide was stirred at 80–90° C. for 3 h. The reaction mixture was diluted with 25% sodium chloride solution and extracted with dichloromethane. After drying and concentration the crude product was purified by column chromatography using silica gel (MN Kieselgel 60) as adsorbent and a mixture of ethyl acetate-methanol (2:1) as eluent to yield 1.34 g (59%) of the title compound; Mp.: 220–221° C.

Example 15

5-(4-Nitrophenyl)-7-(2-thiazolyl)-8,9-dihydro-7H-1,3-dioxolo[4,5-h][2,3]benzodiazepine The title compound was obtained from the starting material VIII and bromoacetaldehyde diethyl acetal according to the method described in Example 1. Mp.: 203–215° C. Yield: 77%.

Example 16

(±)-8-Methyl-5-(3-methyl-4-nitrophenyl)-7-(2-thiazolyl)-8,9-dihydro-7H-1,3-dioxolo[4,5-h][2,3]benzodiazepine The title compound was obtained from the starting material IV according to the method described in Example 1. Mp.: 171–175° C. Yield: 46%.

Example 17

(±)-8-Methyl-5-phenyl-7-(2-thiazolyl)-8,9-dihydro-7H-1,3-dioxolo[4,5-h][2,3]benzodiazepine The title compound was obtained from the starting material VII according to the method described in Example 1. Mp.: 180–184° C. Yield: 51%.

Example 18

(±)-7-Bromo-4-methyl-8-methoxy-1-(4-nitrophenyl)-3-(2-thiazolyl)-4,5-dihydro-3H-[2,3]benzodiazepine The title compound was obtained from the starting material X according to the method described in Example 1. Mp.: 184–190° C. Yield: 54%.

Example 19

(±)-8-Chloro-4-methyl-1-(4-nitrophenyl)-3-(2-thiazolyl)-4,5-dihydro-3H-[2,3]benzodiazepine The title compound was obtained from the starting material V according to the method described in Example 1. Mp.: 213–216° C. Yield: 67%.

Example 20

(±)-8-Chloro-4-methyl-3-(4-methyl-thiazol-2-yl)-1-(4-nitrophenyl)-4,5-dihydro-3H-[2,3]benzodiazepine The title compound was obtained from the starting material V according to the method described in Example 4. Mp.: 209–216° C. Yield: 94%.

Example 21

(±)-3-(4,5-Dihydro-thiazol-2-yl)-8-chloro-4-methyl-1-(4-nitrophenyl)-4,5-dihydro-3H-[2,3]benzodiazepine The title compound was obtained from the starting material V according to the method described in Example 9. Mp.: 225–227° C. Yield: 69%.

Example 22

(±)-3-(4,5-Dihydro-3-oxo-thiazol-2-yl)-8-chloro-4-methyl-1-(4-nitrophenyl)-4,5-dihydro-3H-[2,3]benzodiazepine The title compound was obtained from the starting material V according to the method described in Example 12. Mp.: 226–228° C. Yield: 96%.

Example 23

(±)-7,8-Dichloro-4-methyl-3-(4-methyl-thiazol-2-yl)-1-(4-nitrophenyl)-4,5-dihydro-3H-[2,3]benzodiazepine The title compound was obtained from the starting material VI according to the method described in Example 4. Mp.: 240–242° C. Yield: 77%.

Example 24

(±)-7-(4,5-Dihydro-oxazol-2-yl)-8-methyl-5-(4-nitrophenyl)-8,9-dihydro-7H-1,3-dioxolo[4,5-h][2,3]benzodiazepine A mixture of 1.43 g (3.32 mmol) of the starting material XXV, 1.38 g (9.98 mmol) of anhydrous potassium carbonate, 0.24 g (1.60 mmol) of sodium iodide and 24 ml of dimethylformamide was stirred at 100–110° C. for 4 h. Then the mixture was diluted with water and the precipitated crude product was recrystallized from ethanol to yield 1.00 g (76%) of the title compound; Mp.: 194–196° C.

Example 25

(±)-8-Methyl-5-(4-nitrophenyl)-7-(1,3,4-thiadiazol-2-yl)-8,9-dihydro-7H-1,3-dioxolo[4,5-h][2,3]benzodiazepine A mixture of 0.57 g (1.43 mmol) of the starting material XVIII, 6 ml of triethyl orthoformate and a catalytic amount of hydrochloric acid was stirred at 80° C. for 1 h. After cooling the precipitated crystals were filtered off, washed with ethanol and dried to yield 0.45 g (77%) of the title compound; Mp.: 212–213° C.

Example 26

(R)-8-Methyl-5-(4-nitrophenyl)-7-(1,3,4-thiadiazol-2-yl)-8,9-dihydro-7H-1,3-dioxolo[4,5-h][2,3]benzodiazepine The title compound was obtained from the starting material XIX according to the method described in Example 25. Mp.: 144–147° C. (ethanol-water). Yield: 88%, $[\alpha]_D$: +428° (c=0.2; CHCl$_3$).

Example 27

(±)-8-Methyl-7-(5-methyl-1,3,4-thiadiazol-2-yl)-5-(4-nitrophenyl)-8,9-dihydro-7H-1,3-dioxolo[4,5-h][2,3]benzodiazepine To an ice cooled stirred mixture of 1.0 g (2.50 mmol) of the starting material XVIII, 35 ml of dichloromethane, 0.40 ml (2.75 mmol) of triethylamine and 0.22 ml (2.80 mmol) of acetyl chloride was added. The so obtained solution was left at room temperature for 16 h, then 0.6 g of p-toluenesulfonic acid was added and the mire was stirred at 40° C. for 2 h. Then the reaction mixture was washed with sodium hydrogen carbonate solution and water until neutrality, dried and concentrated. The crude product was treated with methanol, then recrystallized from ethanol to yield 0.99 g (91%) of the title compound. Mp.: 213–215° C.

Example 28

(R)-8-Methyl-7-(5-methyl-1,3,4-thiadiazol-2-yl)-5-(4-nitrophenyl)-8,9-dihydro-7-1,3-dioxolo[4,5-h][2,3]benzodiazepine Method A The title compound was obtained from the starting material XIX by carrying out the acylation with acetic anhydride according to the method described in Example 27. The obtained crude product was purified by column chromatography using silica gel (MN Kieselgel 60) as adsorbent and a mixture of n-hexane-ethyl acetate (1:1) as eluent. After concentration of the fractions containing the title compound the residue was treated with isopropyl ether to yield 0.95 g of a solid foam (polymorph). Yield: 89%.

Method B

To a solution of 4.04 g (10.0 mmol) of the starting material XII, 3 ml of dimethylformamide, 1.40 ml (10.0 mmol) of triethylamine and 0.06 g (0.5 mmol) of 4-dimethylaminopyridine 1.48 g (20.0 mmol) of acetic hydrazide was added. The reaction mixture was stirred at 50° C. for 5 h, then diluted with water, the precipitated crystals were filtered off and washed with water. The so obtained 4.5 g of (R)—N'-{8-methyl-5-(4-nitrophenyl)-8,9-dihydro-7H-1,3-dioxolo[4,5-h][2,3]benzodiazepine-7-carbothioyl}-acetic hydrazide according to its $^1$H-NMR spectrum was a mixture of rotation isomers. (The analyzed sample was purified by column chromatography using a mixture of n-hexane-ethyl acetate (1:1) as eluent and it was crystallized with 0.5 mol of ethyl acetate, Mp.: 118° C.).

To a suspension of the above intermediate in 50 ml of ethanol 0.75 ml of concentrated hydrochloric acid was added, and the so obtained solution was refluxed for 2 h. After concentration and treatment with water 4.2 g of a crude product was obtained. Purification by column chromatography using silica gel (MN Kieselgel 60) as adsorbent and a mixture of n-hexane-ethyl acetate as eluent and drying at 60° C. in vacuum yielded the title compound with a melting point of 101–102° C. $[\alpha]_D$: +453° (c=0.5; CHCl$_3$).

The compounds of Examples 29–34 were obtained according to the method described in Example 27 using the appropriate acid chlorides.

Example 29

(±)-7-(5-Cyclopropyl-1,3,4-thiadiazol-2-yl)-8-methyl-5-(4-nitrophenyl)-8,9-dihydro-7H-1,3-dioxolo[4,5-h][2,3]benzodiazepine Mp.: 142–145° C.; yield: 49%.

Example 30

(±)-7-(5-Ethyl-1,3,4-thiadiazol-2-yl)-8-methyl-5-(4-nitrophenyl)-8,9-dihydro-7H-1,3-dioxolo[4,5-h][2,3]benzodiazepine Mp.: 163–164° C.; yield: 84%.

Example 31

(R)-7-(5-Ethyl-1,3,4-thiadiazol-2-yl)-8-methyl-5-(4-nitrophenyl)-8,9-dihydro-7H-1,3-dioxolo[4,5-h][2,3]benzodiazepine Mp.: 105° C.; yield: 63%. $[\alpha]_D$: +418° (c=0.5; CHCl$_3$).

Example 32

(±)-8-Methyl-5-(4-nitrophenyl)-7-(5-trifluoromethyl-1,3,4-thiadiazol-2-yl)-8,9-dihydro-7H-1,3-dioxolo[4,5-h][2,3]benzodiazepine Mp.: 184–185° C.; yield: 67%.

Example 33

(±)-8-Methyl-5-(4-nitrophenyl)-7-(5-phenyl-1,3,4-thiadiazol-2-yl)-8,9-dihydro-7H-1,3-dioxolo[4,5-h][2,3]benzodiazepine Mp.: 210–212° C.; yield: 56%.

Example 34

(±)-7-(5-Chloromethyl-1,3,4-thiadiazol-2-yl)-8-methyl-5-(4-nitrophenyl)-8,9-dihydro-7H-1,3-dioxolo[4,5-h][2,3]benzodiazepine Mp.: 210–211° C.; yield: 64%.

Example 35

(±)-7-(5-Cyclopropylaminomethyl-1,3,4-thiadiazol-2-yl)-5-(4-nitrophenyl)-8,9-dihydro-7H-1,3-dioxolo[4,5-h][2,3]benzodiazepine A mixture of 5 ml of dimethylformamide, 0.44 g (0.96 mmol) of (±)-7-(5-chloromethyl-1,3,4-thiadiazol-2-yl)-8-methyl-5-(4-nitrophenyl)-8,9-dihydro-7H-1,3-dioxolo[4,5-h][2,3]benzodiazepine (Example 34) and 0.37 ml (5.31 mmol) of cyclopropylamine was stirred at 70–80° C. for 1 h. Then the reaction mixture was poured into 20% sodium chloride solution and, the precipitated crude product was extracted into ethyl acetate. The solution was washed with water, dried and after evaporation yielded 0.39 g (85%) of the title compound, as solid foam.

Example 36

(±)-8-Chloro-4-methyl-1-(4-nitrophenyl)-3-(1,3,4-thiadiazol-2-yl)-4,5-dihydro-3H-[2,3]benzodiazepine The title compound was obtained from the starting material XX according to the method described in Example 25. Mp.: 188° C., yield: 86%.

Example 37

(±)-8-Chloro-4-methyl-3-(5-methyl-1,3,4-thiadiazol-2-yl)-1-(4-nitrophenyl)-4,5-dihydro-3H-[2,3]benzodiazepine The title compound was obtained from the starting material XX according to the method described in Example 27. Mp.: 162–164° C.; yield: 52%.

Example 38

(±)-8-Methyl-5-(3-methyl-4-nitrophenyl)-7-(5-methyl-1,3,4-thiadiazol-2-yl)-8,9-dihydro-7H-1,3-dioxolo[4,5-h][2,3]benzodiazepine The title compound was obtained from the starting material XXII according to the process described in method A of Example 28. Mp.: 228–240° C.; yield: 74%.

Example 39

(±)-8-Methyl-5-(4-methyl-3-nitrophenyl)-7-(5-methyl-1,3,4-thiadiazol-5-yl)-8,9-dihydro-7H-1,3-dioxolo[4,5-h][2,3]benzodiazepine The title compound was obtained from the starting material XV according to the process described in method B of Example 28. Mp.: 220° C. (ethanol); yield: 57%.

Example 40

(±)-8-Methyl-7-(5-methyl-1,3,4-thiadiazol-2-yl)-5-(3-nitrophenyl)-8,9-dihydro-7H-1,3-dioxolo[4,5-h][2,3]benzodiazepine The title compound was obtained from the starting material XIII according to the process described in method B of Example 28. Mp.: 118–119° C.; yield: 67%.

Example 41

(±)-7-Bromo-4-methyl-3-(5-methyl-1,3,4-thiadiazol-2-yl)-8-methoxy-1-(4-nitrophenyl)-4,5-dihydro-3H-[2,3]benzodiazepine The title compound was obtained from the starting material XXI according to the process described in method A of Example 28. Mp.: 229–233° C.; yield: 76%.

Example 42

(±)-8-Methyl-7-(5-methyl-6H-1,3,4-thiadiazin-2-yl)-5-(4-nitrophenyl)-8,9-dihydro-7H-1,3-dioxolo[4,5-h][2,3]benzodiazepine A mixture of 1.00 g (2.50 mmol) of the starting material XVIII, 20 ml of dimethylformamide and 0.57 g (6.16 mmol) of chloroacetone was stirred at room temperature for 2 h. After dilution with water the precipitated crystals were filtered off and purified by refluxing in ethyl acetate to yield 0.73 g (67%) of the title compound; Mp.: 203–204° C.

Example 43

(±)-7-(5,6-Dihydro-5-oxo-4H-1,3,4-thiadiazin-2-yl)-8-methyl-5-(4-nitrophenyl)-8,9-dihydro-7H-1,3-dioxolo[4,5-h][2,3]benzodiazepine A mixture of 1.00 g (2.50 mmol) of the starting material XVIII, 20 ml of dimethylformamide and 0.94 g (6.14 mmol)

of methyl bromoacetate was stirred at 70° C. for 1.5 h. After dilution with water the precipitated crystals were filtered off and purified by refluxing in ethyl acetate to yield 0.41 g (37%) of the title compound; Mp.: 294–295° C. (dec.).

Example 44

(±)-8-Methyl-5-(4-nitrophenyl)-7-(5-oxo-4,5-dihydro-1,3,4-thiadiazol-2-yl)-8,9-dihydro-7H-1,3-dioxolo[4,5-h][2,3]benzodiazepine A mixture of 2.14 g (4.69 mmol) of the starting material XXX and 122 ml of concentrated hydrochloric acid was stirred at 80° C. A solid material precipitated from the starting solution. The reaction mixture was concentrated to about half of its volume, diluted with 40 ml of water and made alkaline with sodium hydrogen carbonate solution. The precipitated product was filtered off and washed with water to yield 1.40 g (70%) of the title compound. Mp.: 288° C.

Example 45

(R)-8-Methyl-5-(4-nitrophenyl)-7-(5-methyl-1,3,4-oxadiazol-2-yl)-8,9-dihydro-7H-1,3-dioxolo[4,5-h][2,3]benzodiazepine A stirred mixture of 2.2 g (5.15 mmol) of (R)—N'-(8-methyl-5-(4-nitrophenyl)-8,9-dihydro-7H-1,3-dioxolo[4,5-h][2,3]benzodiazepin-7-carbothioyl)-acetic hydrazide (an intermediate of method B of Example 28), 44 ml of ethanol and 1.72 g (5.39 mmol) of mercury (II) acetate was refluxed for 2 h. The residue obtained on concentration was dissolved in dichloromethane and filtered through a neutral aluminum oxide column. After washing the column the filtrate was concentrated and the residue was purified by column chromatography using silica gel (MN Kieselgel 60) as adsorbent and a mixture of n-hexane-ethyl acetate (1:2.5) as eluent to yield 1.07 g (51%) of the title compound. Mp.: 202–204° C. after recrystallization from ethanol. [α]: −249° (c=0.22; CHCl$_3$).

Example 46

(±)-8-Methyl-7-(2-methyl-3-oxo-2,3-dihydro-1,2,4-thiadiazol-5-yl)-5-(4-nitrophenyl)-8,9-dihydro-7H-1,3-dioxolo[4,5-h][2,3]benzodiazepine To an ice cooled stirred solution of 0.44 g (1.0 mmol) of the starting material XXVII in 8 ml of chloroform a solution of 0.19 g (1.2 mmol) of bromine in 3 ml of chloroform was added. After 0.5 h the reaction mixture was diluted with 15 ml of chloroform and washed with sodium hydrogen carbonate solution and water. The residue obtained on concentration was stirred with methanol and filtered to yield 0.36 g (82%) of the title compound. Mp.: 296° C. after recrystallization from ethyl acetate.

The compounds of Example 47 and 48 were obtained analogously from the starting materials XXVIII and XXI, respectively.

Example 47

(±)-7-(2-Cyclopropyl-3-oxo-2,3-dihydro-1,2,4-thiadiazol-5-yl)-8-methyl-5-(4-nitrophenyl)-8,9-dihydro-7H-1,3-dioxolo[4,5-h][2,3]benzodiazepine Mp.: 246–247° C. (ethyl acetate), yield: 64%.

Example 48

(±)-7-(2-Ethyl-3-oxo-2,3-dihydro-1,2,4-thiadiazol-5-yl)-8-methyl-5-(4-nitrophenyl)-8,9-dihydro-7H-1,3-dioxolo[4,5-h][2,3]benzodiazepine Mp.: 250–256° C., yield: 60%.

Example 49

(±)-7-(4-Carboxythiazol-2-yl)-8-methyl-5-(4-nitrophenyl)-8,9-dihydro-7H-1,3-dioxolo[4,5-h][2,3]benzodiazepine A mixture of 9 ml of ethanol, 0.85 g (1.89 mmol) of (±)-7-(4-ethoxycarbonyl-thiazol-2-yl)-8-methyl-5-(4-nitrophenyl)-8,9-dihydro-7H-1,3-dioxolo[4,5-h][2,3]benzodiazepine (Example 8) and 7 ml of 1N sodium hydroxide solution was stirred at 90° C. After cooling, it was acidified with acetic acid, diluted with water and the precipitated crystals were filtered off, washed with water and dried to yield 0.78 g (98%) of the title compound; Mp.: >260° C.

Example 50

(±)-8-Methyl-5-(4-nitrophenyl)-7-(5-tetrazolyl)-8,9-dihydro-7H-1,3-dioxolo[4,5-h][2,3]benzodiazepine A mixture of 0.60 g (1.70 mmol) of the starting material XXIII, 3 ml of dimethylformamide, 0.12 g (1.87 mmol) of sodium azide and 0.10 g (1.87 mmol) of ammonium chloride was stirred at 140° C. for 30 min. The cooled reaction mixture was diluted with water and the precipitated crystals were filtered off. The so obtained product was purified by column chromatography using silica gel (MN Kieselgel 60) as adsorbent and a mixture of chloroform-methanol (99:1) as eluent to yield 0.68 g (54%) of the title compound; Mp.: 263–264° C.

Example 51

(±)-8-Methyl-5-(4-nitrophenyl)-7-(1,2,4-oxadiazol-3-yl)-8,9-dihydro-7H-1,3-dioxolo[4,5-h][2,3]benzodiazepine A mixture of 1.50 g (3.91 mmol) of the starting material XXIV and 15 ml of triethyl orthoformate in the presence of 0.05 ml of 36% hydrochloric acid was stirred at 110° C. for 30 min, then concentrated in vacuum. The residue was stirred with water, the precipitated crystals were filtered off, washed with water and recrystallized from 2-methoxyethanol to yield 1.15 g (75%) of the title compound; Mp.: 190–196° C.

Example 52

(±)-8-Methyl-7-(5-methyl-1,2,4-oxadiazol-3-yl)-5-(4-nitrophenyl)-8,9-dihydro-7H-1,3-dioxolo[4,5-h][2,3]benzodiazepine A mixture of 3.0 g (7.82 mmol) of the starting material XXIV and 15 ml of acetic anhydride was stirred at 110° C. for 1 h, then after cooling it was diluted with water and extracted with dichloromethane. The organic layer was concentrated and the residue was purified by column chromatography using silica gel (MN Kieselgel 60) as adsorbent and a mire of n-hexane-ethyl acetate (2:1) as eluent to yield 1.58 g (50%) of the title compound; Mp.: 191–200° C.

Example 53

(±)-8-Methyl-7-(2-methylthiazol-4-yl)-5-(4-nitrophenyl)-8,9-dihydro-7H-1,3-dioxolo[4,5-h][2,3]benzodiazepine Step A (±)-7-Bromoacetyl-8-methyl-5-(4-nitrophenyl)-8,9-dihydro-7H-1,3-dioxolo[4,5-h][2,3]benxodiazepine A mixture of 4.80 g (14.7 mmol) of the starting material I, 24 ml of dimethylformamide, 2.16 g (15.5 mmol) of bromoacetic acid and 4.56 g (22 mmol) of dicyclohexylcarbodiimide was stirred for 20 h. The reaction mixture was filtered and the filtrate was concentrated. The residue was taken up in ethyl acetate, washed with water, concentrated and recrystallized from ethanol to yield 4.83 g (73%) of the title compound; Mp.: 183–186° C.

Step B

The product obtained in Step A was dissolved in 45 ml of dimethylformamide and after adding 4.96 g (65 mmol) of thioacetamide it was stirred at 80° C. for 1 h, then cooled and poured into water. The precipitated crude product was filtered off, washed with water and purified by column chromatography using silica gel (MN Kieselgel 60) as adsorbent and a mixture of hexane-ethyl acetate (9:1) as eluent to yield 1.67 g (37%) of the tide compound; Mp.: 178–190° C.

Example 54

(±)-8-Methyl-5-(4-nitrophenyl)-7-(2-pyrimidinyl)-8,9-dihydro-7H-1,3-dioxolo[4,5-h][2,3]benzodiazepine Step A 1-{6-[(4-Nitrophenyl)-(pyrimidin-2-yl-hydrazono)-methyl]-benzo-1,3-dioxol-5-yl}-propan-2-ol A stirred mixture of 3.29 g (9.99 mmol) of (±)-7-methyl-5-(4-nitrophenyl)-7,8-dihydro-5H-[1,3]dioxolo[4,5-g]isochroman-5-ol, 40 ml of ethyl acetate and 1.0 ml (1.15 mmol) perchloric acid was refluxed for 1 h. After cooling the precipitated (±)-7-methyl-5-(4-nitrophenyl)-7,8-dihydro-[1,3]dioxolo[4,5-g]isochromen-6-ylium perchlorate was filtered off, and it was stirred at reflux temperature with 1.6 g (14.55 mmol) of 2-hydrazinopyrimdine in 50 ml of isopropanol for 2 h, then concentrated. The residue was dissolved in dichloromethane and washed several times with water. After drying and evaporation the crude product was purified by column chromatography using silica gel (MN Kieselgel 60) as adsorbent and a mixture of toluene-ethyl acetate (0.1:4) as eluent to yield 2.71 g (64%) of the title compound; Mp.: 125–127° C.

Step B

1-{6-[(4-Nitrophenyl)-(pyrimidin-2-yl-hydrazono)-methyl]-benzo-1,3-dioxol-5-yl}-propan-2-ol mesylate 2.35 g (5.58 mmol) of the compound prepared in Step A was dissolved in 50 ml of dry dichloromethane. The solution was cooled to 0° C. and after addition of 2.1 ml (15.07 mmol) of triethylamine 0.87 ml (11.22 mmol) of methanesulfonyl chloride was added over a period of 20 min, then the mixture was stirred at room temperature for 3 h. After washing with water it was dried and concentrated to yield 2.69 g (54%) of the title compound as an intermediate; Mp.: 122–124° C.

Step C

A mixture of 3.13 g (6.27 mmol) of the compound obtained in Step B, 60 ml of a 1:1 mixture of dichloromethane-methanol and 0.52 ml (6.90 mmol) of 50% sodium hydroxide solution was stirred at room for 1.5 h. After filtration the reaction mixture was concentrated, the residue was treated with water and recrystallized from three fold dimethylformamide containing 10% water to yield 1.96 g (77%) of the title compound; Mp.: 261–263° C.

Example 55

(±)-7-(3-Chloropyridazin-6-yl)-8-methyl-5-(4-nitrophenyl)-8,9-dihydro-7H-1,3-dioxolo[4,5-h][2,3]benzodiazepine Step A 1-{6-[(6-Chloropyridazin-3-yl)-hydrazono-(4-nitrophenyl)-methyl]-(benzo-1,3-dioxol-5-yl)}-propan-2-ol A stirred mixture of 2.00 g (6.07 mmol) of (±)-7-methyl-5-(4-nitrophenyl)-7,8-dihydro-5H-[1,3]dioxolo[4,5-g]isochroman-5-ol, 32 ml of isopropanol, 0.3 ml of hydrochloric acid and 1.04 g (7.28 mmol) of 4-hydrazino-6-chloropyridazine was refluxed for 3 h. After diluting with water, the precipitated crystals were filtered off, dried and recrystallized first from ethyl acetate, then from dimethylformamide containing 10% water to yield 1.53 g (55%) of the title compound; Mp.: 135–137° C.

Step B

A mixture of 0.3 g (0.66 mmol) of the compound prepared in Step A, 10 ml of dimethylformamide and 0.34 g (1.30 mmol) of triphenyiphosphine was stirred at room temperature for 5 min, then 0.20 ml (1.27 mmol) of diethyl azodicarboxylate was added and stirring was continued for 24 h. After dilution with sodium chloride solution the precipitated product was filtered off, dried and purified by column chromatography using silica gel (MN Kieselgel 60) as adsorbent and a mixture of chloroform-methanol (99:1) as eluent. The residue obtained on concentration was crystallized by refluxing in ethanol to yield 0.12 g (42%) of the title compound; Mp.: 254–255° C.

Example 56

(±)-8-Methyl-5-(4-nitrophenyl)-7-(1H(2H)-1,2,4-triazol-3-yl)-8,9-dihydro-7H-1,3-dioxolo[4,5-h][2,3]benzodiazepine Step A (±)-8-Methyl-5-(4-nitrophenyl)-8,9-dihydro-7H-1,3-dioxolo[4,5-h][2,3]benzodiazepine-7-S-methyl-thiocarboximidate The title compound was obtained from the starting material I in dimethylformamide with methyl iodide in the presence of potassium carbonate at room temperature. Mp.: 191–192° C. yield: 94%.

Step B

A mixture of 3.0 g (7.53 mmol) of the compound obtained in Step A, 110 ml of 2-methoxyethanol and 4.50 g (74.93 mmol) of formic hydrazide was stirred at 110° C. in the presence of catalytic amount of p-toluenesulfonic acid for 16 h. The residue obtained on concentration was treated with 10% sodium carbonate solution, the obtained crude product was filtered, dried and purified by column chromatography using silica gel (MN Kieselgel 60) as adsorbent and a mixture of hexane-ethyl acetate (1:2) as eluent to yield 1.86 g (63%) of the title compound; Mp.: 154–156° C.

Example 57

(±)-8-Methyl-7-(5-methyl-2(1)H-1,2,4-triazol-3-yl)-5-(4-nitrophenyl)-8,9-dihydro-7H-1,3-dioxolo[4,5-h][2,3]benzodiazepine A mixture of 15 ml of 2-methoxyethanol, 0.41 g (1.03 mmol) of (±)-8-methyl-5-(4-nitrophenyl)-8,9-dihydro-7H-1,3-dioxolo[4,5-h][2,3]benzodiazepine-7-S-methyl-thiocarboximidate (Step A of Example 56) and 0.35 g (4.68 mmol) of acetic hydrazide was stirred at 110° C. in the presence of catalytic amount of p-toluenesulfonic acid for 16 h. The residue obtained on concentration was treated with 10% sodium carbonate solution, the obtained crude product was filtered, dried and purified by column chromatography using silica gel (MN Kieselgel 60) as adsorbent and a mixture of hexane-ethyl acetate (1:2) as eluent to yield 0.32 g (78%) of the title compound; Mp.: 144–147° C. (solid foam).

Example 58

(±)-7-(1,5-Dimethyl-1H-1,2,4-triazol-3-yl)-8-methyl-5-(4-nitrophenyl)-8,9-dihydro-7H-1,3-dioxolo[4,5-h][2,3]benzodiazepine (isomer I) and (±)-7-(2,5-dimethyl-2H-1,2,4-triazol-3-yl)-8-methyl-5-(4-nitrophenyl)-8,9-dihydro-7H-1,3-dioxolo[4,5-h][2,3]benzodiazepine (isomer II)

A mixture of 0.57 g (5.08 mmol) of potassium tert-butoxide, 2.05 g (5.04 mmol) of (±)-8-methyl-7-(5-methyl-2(1)H-1,2,4-triazol-3-yl)-5-(4-nitrophenyl)-8,9-dihydro-7H-1,3-dioxolo[4,5-h][2,3]benzodiazepine (Example 57), 40 ml of tetrahydrofuran and 0.32 ml (5.14 mmol) of methyl iodide was stirred at room temperature for 16 h. then the reaction mixture was diluted with water, extracted with ethyl acetate, the organic layer was dried and concentrated. The two products formed in the reaction were separated by column chromatography using silica gel (MN Kieselgel 60) as adsorbent and ethyl acetate as eluent. Isomer II, having $R_F$: 0.55 was first obtained, which was refluxed in ethanol to yield 0.30 g (14%), Mp.: 185–187° C. Then isomer I was collected, having $R_F$: 0.26, which after refluxing in ethanol weighed 0.67 g (32%), Mp.: 193–195° C.

Example 59

(±)-8-Methyl-7-(1-methyl-1H-1,2,4-triazol-3-yl)-5-(4-nitrophenyl)-8,9-dihydro-7H-1,3-dioxolo[4,5-h][2,3]benzodiazepine (isomer I) and (±)-8-methyl-7-(2-methyl-2H-1,2,4-triazol-3-yl)-5-(4-nitrophenyl)-8,9-dihydro-7H-1,3-dioxolo[4,5-h][2,3]benzodiazepine (isomer II)

A mixture of 0.41 g (3.65 mmol) of potassium tert-butoxide, 1.4 g (3.57 mmol) of (±)-8-methyl-5-(4-nitrophenyl)-7-(1H(2H-1,2,4-triazol-3-yl)-8,9-dihydro-7H-1,3-dioxolo[4,5-h][2,3]benzodiazepine (Example 56), 35 ml of tetrahydrofuran and 0.23 ml (3.69 mmol) of methyl iodide was stirred at room temperature for 16 h. After dilution with water the reaction mixture was extracted with ethyl acetate, the organic layer was dried and concentrated. The two products formed in the reaction were separated by column chromatography using silica gel (MN Kieselgel 60) as adsorbent and ethyl acetate as eluent. Isomer I, having $R_F$: 0.22, weighed 0.37 g, yield: 26%, Mp.: 115–117° C. Isomer II, having $R_F$: 0.63, was 0.35 g, yield: 24%, Mp.: 92–94° C.

Examples 60–119

General Procedures for Reduction of the Nitro Groups of the Compounds Obtained in the Above Examples Method A 2.0 mmol of nitro compound was dissolved in a mixture of methanol-dichloromethane and after adding 6–10 mmol of 85–98% hydrazine hydrate and 0.1–2 g RaNi catalyst the mixture was stirred at 20–40° C. for 1–5 h. After filtration of the catalyst the filtrate was concentrated, the residue was treated with water and the product was filtered off.

Method B 5.5 g of RaNi catalyst was prehydrogenated in 250 ml of a 2:1 mixture of methanol-dichloromethane, then 20.0 mmol of nitro compound was added in 250 ml of the above solvent mixture and the so obtained mixture was hydrogenated at atmospheric pressure. After filtration of the catalyst the filtrate was concentrated, the residue was treated with water, the product was filtered, washed and dried.

Method C

A stirred mixture of 1.82 mmol of nitro compound, 30 ml of ethanol and 2.46 g (10.91 mmol) of tin (II) chloride dihydrate was refluxed for 3 h. The reaction mixture was concentrated, then aqueous sodium hydrogen carbonate and ethyl acetate were added to the residue. After separation the water phase was extracted with ethyl acetate, the combined organic layers were washed with sodium chloride solution, dried and concentrated. If necessary the residue was purified either by column chromatography or by recrystallization.

Method D 3.4 mmol of nitro compound was dissolved in 35 ml of a mixture of methanol-dichloromethane (1:1), 0.4 g of a 10% palladium on activated carbon catalyst and 0.47 g of potassium carbonate were added and the so obtained mixture was hydrogenated in the presence of 1 ml of water. After completion of the reaction the catalyst was filtered off, the filtrate was concentrated, the residue was treated with water and filtered.

Method E 4.0 mmol of nitro compound was dissolved in 48 ml of methanol containing 5% water, then after addition of 0.20 g of the catalyst 10% palladium on activated carbon 3.5 equivalent of a concentrated aqueous solution of potassium formate was added dropwise at room temperature and the mixture was stirred at the above temperature. After completion of the reaction the catalyst was filtered off, the filtrate was concentrated, the residue is treated with water and filtered.

TABLE 10

2,3-Benzodiazepines containing aminophenyl group
(The $^1$H NMR spectra were recorded at 250 MHz unless stated otherwise)

| Number of Example | Name | Mp. (° C.) Solvent of recrystall. | Yield (%) $[\alpha]_D$ |
|---|---|---|---|
| 60 | (±)-5-(4-Aminophenyl)-8-methyl-7-(2-thiazolyl)-8,9-dihydro-7H-1,3-dioxolo[4,5-h][2,3]benzodiazepine | 187–190 | 78 |
| Method A | $^1$H NMR (CDCl$_3$) δ 1.32(3H, d, 6.5Hz), 2.78(1H, dd, 14.0Hz, 9.7Hz), 2.97(1H, dd, 14.0Hz, 4.9Hz), 3.80(2H, br), 5.26(1H, m), 5.98(2H, m), 6.65(1H, s), 6.67(1H, d, 4.0Hz), 6.73 (2H, dm), 6.80(1H, s), 7.37(1H, d, 4.0Hz), 7.55(2H, dm) MS: EI(70 eV): [M]$^+$: 378, m/z: 363, 279, 278, 253, 252 | | |
| 61 | (R)-5-(4-Aminophenyl)-8-methyl-7-(2-thiazolyl)-8,9-dihydro-7H-1,3-dioxolo[4,5-h][2,3]benzodiazepine | 125–130 | 84 −578° (c = 1, CHCl$_3$) |
| Method A | $^1$H NMR (CDCl$_3$) δ 1.29(3H, d, 6.5Hz), 2.77(1H, dd, 14.0Hz, 9.7Hz), 3.00(1H, dd, 14.0Hz, 4.9Hz), 3.92(2H, br), 5.23(1H, m), 5.98(2H, m), 6.62(1H, d, 4.0Hz), 6.65(1H, s), 6.72 (2H, dm), 6.80(1H, s), 7.32(1H, d, 4.0Hz), 7.55(2H, dm) | | |
| 62 | (S)-5-(4-Aminophenyl)-8-methyl-7-(2-thiazolyl)-8,9-dihydro-7H-1,3-dioxolo[4,5-h][2,3]benzodiazepine | 124–128 | 94 +546° (c = 0.34, CHCl$_3$) |
| Method A | $^1$H NMR (DMSO-d$_6$) δ 1.15(3H, d, 6.5Hz), 2.60(1H, dd, 13.6Hz, 10.5Hz), 2.94(1H, dd, 13.6Hz, 4.8Hz), 4.99(1H, m), 5.72(2H, br), 6.03(2H, m), 6.60(2H, dm), 6.62(1H, s), 6.81 (1H, d, 4.0Hz), 7.04(1H, s), 7.27(1H, d, 4.0Hz), 7.55(2H, dm) MS: EI(70 eV): [M]$^+$: 378, m/z: 377, 363, 279, 278, 253, 252 CI: [M + H]$^+$: 379, [M]$^+$: 378, m/z: 363 | | |
| 63 | (±)-5-(4-Aminophenyl)-8-methyl-7-(4-methyl-thiazol-2-yl)-8,9-dihydro-7H-1,3-dioxolo-[4,5-h][2,3]benzodiazepine | 190–191 (EtOH) | 65 |
| Method A | $^1$H NMR (CDCl$_3$) δ 1.30(3H, d, 6.5Hz), 2.29(3H, s), 2.77(1H, dd, 14.0Hz, 10.0Hz), 2.92 (1H, dd, 14.0Hz, 5.1Hz), 3.94(2H, br), 5.27(1H, m), 5.97(2H, m), 6.20(1H, s), 6.53(2H, dm), 6.70(1H, s), 6.88(1H, s), 7.53(2H, dm) | | |
| 64 | (±)-5-(4-Aminophenyl)-8-methyl-7-(5-methyl-thiazol-2-yl)-8,9-dihydro-7H-1,3-dioxolo-[4,5-h][2,3]benzodiazepine | 165–167 | 47 |
| Method A | $^1$H NMR (DMSO-d$_6$) δ 1.17(3H, d, 6.5Hz), 2.25(3H, s), 2.60(1H, dd, 13.9Hz, 10.3Hz), 2.94(1H, dd, 13.9Hz, 5.1Hz), 4.95(1H, m), 5.70(2H, br), 6.05(2H, dm), 6.57(1H, s), 6.62 (2H, dm), 6.93(1H, s), 7.04(1H, s), 7.36(2H, dm) | | |
| 65 | (±)-5-(4-Aminophenyl)-8-methyl-7-(4,5-dimethyl-thiazol-2-yl)-8,9-dihydro-7H-1,3-dioxolo-[4,5-h][2,3]benzodiazepine | 240–242 (EtOH) | 83 |
| Method A | $^1$H NMR (DMSO-d$_6$) δ 1.16(3H, d, 6.5Hz), 2.06(3H, s), 2.13(3H, s), 2.62(1H, dd, 14.0Hz, 10.0Hz), 2.92(1H, dd, 14.0Hz, 5.0Hz), 4.97(1H, m), 5.70(2H, br), 6.04(2H, dm), 6.60(1H, s), 6.62(2H, dm), 7.02(1H, s), 7.34(2H, dm) | | |
| 66 | (±)-5-(4-Aminophenyl)-7-(4-phenyl-thiazol-2-yl)-8-methyl-8,9-dihydro-7H-1,3-dioxolo-[4,5-h][2,3]benzodiazepine | 221–223 (EtOH) | 89 |
| Method A | $^1$H NMR (CDCl$_3$) δ 1.29(3H, d, 6.5Hz), 2.80(1H, dd, 14.0Hz, 9.4Hz), 3.00(1H, dd, 14.0Hz, 4.8Hz), 3.93(2H, br), 5.40(1H, m), 5.98(2H, m), 6.62(1H, s), 6.70(2H, dm), 6.78(1H, s), 7.29(1H, t), 7.39(1H, t), 7.50(1H, s), 7.57(2H, dm), 7.86(2H, d) | | |
| 67 | (±)-5-(4-Aminophenyl)-7-(4-ethoxycarbonyl-thiazol-2-yl)-8-methyl-8,9-dihydro-7H-1,3-dioxolo-[4,5-h][2,3]benzodiazepine | 251–252 (EtOH) | 83 |
| Method A | $^1$H NMR (CDCl$_3$) δ 1.29(3H, d, 6.5Hz), 1.38(3H, t), 2.76(1H, dd, 14.0Hz, 10.0Hz), 2.92 (1H, dd, 14.0Hz, 5.0Hz), 3.98(2H, br), 4.33(2H, q), 5.40(1H, m), 6.00(2H, m), 6.68(1H, s), 6.69(2H, dm), 6.82(1H, s), 6.86(1H, s), 7.51(2H, dm) | | |
| 68 | (±)-5-(4-Aminophenyl)-7-(4,5-dihydro-thiazol-2-yl)-8-methyl-8,9-dihydro-7H-1,3-dioxolo-[4,5-h][2,3]benzodiazepine | 145–150 (EtOH) | 84 |
| Method A | $^1$H NMR (CDCl$_3$) δ 1.21(3H, d, 6.5Hz), 2.70(1H, dd, 14.0Hz, 10.0Hz), 2.96(1H, dd, 14.0Hz, 5.0Hz), 3.20(1H, m), 3.70(1H, m), 3.90(2H, br), 4.17(2H, m), 5.09(1H, m), 5.98(2H, dm), 6.60(1H, s), 6.66(2H, dm), 6.73(1H, s), 7.47(2H, dm) MS: EI(70 eV): [M]$^+$: 380, m/z: 365, 339, 279, 264, 253, 252 | | |
| 69 | (R)-5-(4-Aminophenyl)-7-(4,5-dihydro-thiazol-2-yl)-8-methyl-8,9-dihydro-7H-1,3-dioxolo-[4,5-h][2,3]benzodiazepine | 148–150 (EtOH) | 82 −239° (c = 0.5, CHCl$_3$) |
| Method A | $^1$H NMR (DMSO-d$_6$) δ 1.16(3H, d, 6.5Hz), 2.60(1H, dd, 14.0Hz, 10.0Hz), 2.90(1H, dd, 14.0Hz, 4.0Hz), 3.25(2H, m), 4.00(2H, m), 4.82(1H, m), 5.73(2H, br), 6.07(2H, dm), 6.64 (s), 6.64(2H, dm), 7.02(1H, s), 7.30(2H, dm) MS: EI(70 eV): [M]$^+$: 380, m/z: 365, 339, 279, 278, 264, 253, 252 CI: [M + H]$^+$: 381, [M]$^+$: 380, m/z: 279 | | |
| 70 | (S)-5-(4-Aminophenyl)-7-(4,5-dihydro-thiazol-2-yl)-8-methyl-8,9-dihydro-7H-1,3-dioxolo-[4,5-h][2,3]benzodiazepine | 150–152 | 92 +175° (c = 0.51, CHCl$_3$) |
| Method A | MS: EI(70 eV): [M]$^+$: 380, m/z: 365, 339, 279, 278, 264, 253, 252 CI: [M + H]$^+$: 381, [M]$^+$: 380, m/z: 279 | | |

TABLE 10-continued 2,3-Benzodiazepines containing aminophenyl group
(The $^1$H NMR spectra were recorded at 250 MHz unless stated otherwise)

| Number of Example | Name | Mp. (° C.) Solvent of recrystall. | Yield (%) $[\alpha]_D$ |
|---|---|---|---|
| 71 | (±)-5-(4-Aminophenyl)-7-(4,5-dihydro-4-oxo-thiazol-2-yl)-8-methyl-8,9-dihydro-7H-1,3-dioxolo-[4,5-h][2,3]benzodiazepine | 218–220 (EtOH) | 85 |
| Method A | $^1$H NMR (DMSO-d$_6$) δ 1.29(3H, d, 6.5Hz), 2.61(1H, dd, 13.0Hz, 12.0Hz), 2.96(1H, dd, 13.0Hz, 5.0Hz), 3.72(2H, m), 5.08(1H, m), 6.01(2H, br), 6.06(2H, dm), 6.60(2H, dm), 6.62(1H, s), 7.10(1H, s), 7.40(2H, dm) | | |
| 72 | (±)-5-(4-Aminophenyl)-7-(4,5-dihydro-5-methyl-4-oxo-thiazol-2-yl)-8-methyl-8,9-dihydro-7H-1,3-dioxolo-[4,5-h][2,3]benzodiazepine | 200–204 (EtOH) | 63 |
| Method A | $^1$H NMR (DMSO-d$_6$) δ 1.32(d) and 1.45(d, overlapping, diastereomers), 2.60(1H, dd, 13.0Hz, 12.0Hz), 2.94(1H, dd, 13.0Hz, 5.0Hz), 3.96 and 4.05(1H, q), 5.08(1H, m), 6.0(2H, br), 6.07(2H, dm), 6.60(2H, dm), 6.62(1H, s), 7.08(1H, s), 7.40(2H, dm)<br>MS: EI(70 eV): [M]$^+$: 408, m/z: 393, 279, 265, 253, 252 | | |
| 73 | (±)-5-(4-Aminophenyl)-7-(5,6-dihydro-4-oxo-4H-1,3-thiazin-2-yl)-8-methyl-8,9-dihydro-7H-1,3-dioxolo-[4,5-h][2,3]benzodiazepine | 226–228 (EtOH) | 90 |
| Method A | $^1$H NMR (DMSO-d$_6$) δ 1.25(3H, d, 6.5Hz), 2.35(2H, m), 2.57(1H, dd, 13.0Hz, 12.0Hz), 2.88(1H, dd, 13.0Hz, 4.0Hz), 3.05(2H, m), 5.21(1H, m), 5.97(2H, br), 6.09(2H, dm), 6.60 (1H, s), 6.62(2H, dm), 7.04(1H, s), 7.42(2H, dm)<br>MS: EI(70 eV): [M]$^+$: 408, m/z: 295, 279, 253, 252 | | |
| 74 | 5-(4-Aminophenyl)-7-(2-thiazolyl)-8,9-dihydro-7H-1,3-dioxolo[4,5-h][2,3]benzodiazepine | 200–204 | 52 |
| Method A | $^1$H NMR (DMSO-d$_6$) δ 2.88(2H, t), 4.21(2H, t), 5.70(2H, s), 6.08(2H, s), 6.60(1H, s), 6.62 (2H, dm), 6.89(1H, d, 4.0Hz), 7.08(1H, s), 7.28(1H, d, 4.0Hz), 7.37(2H, dm) | | |
| 75 | (±)-5-(4-Amino-3-methylphenyl)-8-methyl-7-(2-thiazolyl)-8,9-dihydro-7H-1,3-dioxolo-[4,5-h][2,3]benzodiazepine | 225–227 | 78 |
| Method B | MS: EI(70 eV): [M]$^+$: 392, m/z: 377, 293, 266<br>CI: [M + H]$^+$: 393, [M]$^+$: 392, m/z: 266 | | |
| 76 | (±)-1-(4-Aminophenyl)-4-methyl-8-methoxy-3-(2-thiazolyl)-4,5-dihydro-3H-[2,3]benzodiazepine | 105–107 | 57 |
| Method D | MS: EI(70 eV): [M]$^+$: 364, m/z: 349, 265, 223<br>CI: [M + H]$^+$: 365, [M]$^+$: 364 | | |
| 77 | (±)-1-(4-Aminophenyl)-8-chloro-4-methyl-3-(2-thiazolyl)-4,5-dihydro-3H-[2,3]benzodiazepine | 104–107 | 72 |
| Method A | $^1$H NMR (CDCl$_3$) δ 1.31(3H, d, 6.5Hz), 2.96(1H, dd, 13.0Hz, 10.0Hz), 3.10(1H, dd, 13.0Hz, 5.0Hz), 5.35(1H, m), 6.68(1H, d, 4.0Hz), 6.72(2H, dm), 7.21(1H, d, 4.0Hz), 7.25(1H, d, 1.0Hz), 7.27(1H, d, 7.0Hz), 7.34(1H, dd), 7.53(2H, dm) | | |
| 78 | (±)-1-(4-Aminophenyl)-8-chloro-4-methyl-3-(4-methyl-thiazol-2-yl)-4,5-dihydro-3H-[2,3]benzodiazepine | 173–175 | 90 |
| Method A | $^1$H NMR (CDCl$_3$) δ 1.26(3H, d, 6.5Hz), 2.27(3H, d, 1.0Hz), 2.81(1H, dd, 14.0Hz, 9.7Hz), 3.02(1H, dd, 14.0Hz, 5.0Hz), 3.95(2H, br), 5.28(1H, m), 6.20(1H, q, 1.0Hz), 6.70(2H, dm), 7.17(1H, d, 2.2Hz), 7.22(1H, d, 8.2Hz), 7.33(1H, dd, 8.2Hz, 2.2Hz), 7.51(2H, dm) | | |
| 79 | (±)-1-(4-Aminophenyl)-3-(4,5-dihydro-thiazol-2-yl)-8-chloro-4-methyl-4,5-dihydro-3H-[2,3]benzodiazepine | 213–216 (MeOH) | 79 |
| Method A | $^1$H NMR (DMSO-d$_6$) δ 1.08(3H, d, 6.5Hz), 2.68(1H, dd, 14.0Hz, 10.0Hz), 3.06(1H, dd, 14.0Hz, 5.0Hz), 3.20(2H, m), 4.02(2H, m), 5.68(2H, s), 4.92(1H, m), 6.60(2H, dm), 7.09 (1H, d, 1.0Hz), 7.28(2H, dm), 7.41(1H, d, 7.0Hz), 7.48(1H, dd) | | |
| 80 | (±)-1-(4-Aminophenyl)-3-(4,5-dihydro-4-oxo-thiazol-2-yl)-8-chloro-4-methyl-4,5-dihydro-3H-[2,3]benzodiazepine | 226–228 (iPrOH) | 75 |
| Method A | $^1$H NMR (DMSO-d$_6$) δ 1.32(3H, d, 6.5Hz), 2.68(1H, dd, 13.8Hz, 12.0Hz), 3.08(1H, dd, 13.8Hz, 4.8Hz), 3.77(2H, m), 5.10(1H, m), 6.12(2H, br), 6.66(2H, dm), 7.17(1H, d, 2.0Hz), 7.41(2H, dm), 7.52(1H, d, 8.0Hz), 7.54(1H, dd, 8.0Hz, 2.0Hz) | | |
| 81 | (±)-1-(4-Aminophenyl)-7,8-dichloro-3-(4-methyl-thiazol-2-yl)-4-methyl-4,5-dihydro-3H-[2,3]benzodiazepine | 182–184 (EtOH) | 48 |
| Method A | $^1$H NMR (CDCl$_3$) δ 1.28(3H, d, 6.5Hz), 2.30(3H, s), 2.80(1H, dd, 14.0Hz, 9.6Hz), 3.02 (1H, dd, 14.0Hz, 4.9Hz), 3.96(2H, br), 5.31(1H, m), 6.22(1H, q, 1.0Hz), 6.69(2H, dm), 7.28(1H, s), 7.39(1H, s), 7.50(2H, dm) | | |
| 82 | (±)-5-(4-Aminophenyl)-7-(4,5-dihydro-oxazol-2-yl)-8-methyl-8,9-dihydro-7H-1,3-dioxolo-[4,5-h][2,3]benzodiazepine | 166–167 (EtOH) | 87 |
| Method A | $^1$H NMR (DMSO-d$_6$) δ 1.20(3H, d, 6.5Hz), 2.31(1H, dd, 13.8Hz, 12.0Hz), 2.78(1H, dd, 13.8Hz, 5.8Hz), 3.61(2H, m), 4.18(2H, m), 4.51(1H, m), 5.66(2H, br), 6.03(2H, dm), 6.51 (1H, s), 6.53(2H, dm), 6.98(1H, s), 7.30(2H, dm)<br>MS: EI(70 eV): [M]$^+$: 364, m/z: 349, 323, 279, 278, 252<br>CI: [M + H]$^+$: 365, [M]$^+$: 364 | | |
| 83 | (±)-5-(4-Aminophenyl)-8-methyl-7-(1,3,4-thiadiazol-2-yl)-8,9-dihydro-7H-1,3-dioxolo-[4,5-h][2,3]benzodiazepine | 192–194 (50% EtOH—H$_2$O) | 77 |

TABLE 10-continued 2,3-Benzodiazepines containing aminophenyl group
(The ¹H NMR spectra were recorded at 250 MHz unless stated otherwise)

| Number of Example | Name | Mp. (° C.) Solvent of recrystall. | Yield (%) $[\alpha]_D$ |
|---|---|---|---|
| Method A | ¹H NMR (DMSO-$d_6$) δ 1.20(3H, d, 6.5Hz), 2.62(1H, dd, 13.9Hz, 10.8Hz), 2.99(1H, dd, 13.9Hz, 5.2Hz), 5.01(1H, m), 5.78(2H, br), 6.03(2H, dm), 6.58(1H, s), 6.60(2H, dm), 7.07 (1H, s), 7.32(2H, dm,) | | |
| 84 | (R)-5-(4-Aminophenyl)-8-methyl-7-(1,3,4-thiadiazol-2-yl)-8,9-dihydro-7H-1,3-dioxolo-[4,5-h][2,3]benzodiazepine | 219–220 (ethyl formate) | 67 −490° (c = 0.9, CHCl₃) |
| Method C | ¹H NMR (CDCl₃) δ 1.33(3H, d, 6.5Hz), 2.80(1H, dd, 14.0Hz, 9.9Hz), 2.97(1H, dd, 14.0Hz, 5.0Hz), 4.02(2H, br), 5.30(1H, m), 5.98(2H, dm), 6.65(1H, s), 6.68(2H, dm), 6.80(1H, s), 7.51(2H, dm,), 8.50(1H, s) | | |
| 85 | (±)-5-(4-Aminophenyl)-8-methyl-7-(5-methyl-1,3,4-thiadiazol-2-yl)-8,9-dihydro-7H-1,3-dioxolo-[4,5-h][2,3]benzodiazepine | 143–148 | 89 |
| Method A | ¹H NMR (CDCl₃) δ 1.32(3H, d, 6.5Hz), 2.56(3H, s), 2.76(1H, dd, 14.0Hz, 10.0Hz), 2.93 (1H, dd, 14.0Hz, 5.0Hz), 4.00(2H, br), 5.19(1H, m), 5.98(2H, dm), 6.64(1H, s), 6.70(2H, dm), 6.79(1H, s), 7.48(2H, dm,) MS: EI(70 eV): [M]⁺: 393, m/z: 378, 279, 278, 253, 252 CI: [M + H]⁺: 394, [M]⁺: 393, m/z: 252 | | |
| 86 | (R)-5-(4-Aminophenyl)-8-methyl-7-(5-methyl-1,3,4-thiadiazol-2-yl)-8,9-dihydro-7H-1,3-dioxolo-[4,5-h][2,3]benzodiazepine | 168–170 (50% EtOH—H₂O) | 78 −482° (c = 0.5, CHCl₃) |
| Method B, C | ¹H NMR (DMSO-$d_6$) δ 1.23(3H, d, 6.5Hz), 2.50(3H, s), 2.60(1H, dd, 13.8Hz, 9.6Hz), 2.97 (1H, dd, 13.8Hz, 4.9Hz), 4.93(1H, m), 5.78(2H, br), 6.03(2H, dm), 6.58(1H, s), 6.60(2H, dm), 7.09(1H, s), 7.31(2H, dm) | | |
| 87 | (±)-5-(4-Aminophenyl)-7-(5-cyclopropyl-1,3,4-thiadiazol-2-yl)-8-methyl-8,9-dihydro-7H-1,3-dioxolo[4,5-h][2,3]benzodiazepine | 145–148 (precipit. with water) | 75 |
| Method A | ¹H NMR (DMSO-$d_6$) δ 0.88(2H, m), 1.05(2H, m), 1.22(3H, d, 6.5Hz), 2.22(1H, m), 2.61 (1H, dd, 14.0Hz, 10.0Hz), 2.99(1H, dd, 14.0Hz, 5.0Hz), 4.97(1H, m), 5.78(2H, br), 6.05 (2H, dm), 6.60(1H, s), 6.63(2H, dm), 7.06(1H, s), 7.36(2H, dm) | | |
| 88 | (±)-5-(4-Aminophenyl)-7-(5-ethyl-1,3,4-thiadiazol-2-yl)-8-methyl-8,9-dihydro-7H-1,3-dioxolo-[4,5-h][2,3]benzodiazepine | 135–138 | 67 |
| Method A | ¹H NMR (CDCl₃) δ 1.35(3H, t), 1.36(3H, d, 6.5Hz), 2.79(1H, dd, 14.0Hz, 10.0Hz), 2.98 (2H, q), 2.99(1H, dd, 14.0Hz, 5.0Hz), 3.98(2H, br), 5.25(1H, m), 6.02(2H, dm), 6.63(1H, s), 6.73(2H, dm), 6.82(1H, s), 7.51(2H, dm,) | | |
| 89 | (R)-5-(4-Aminophenyl)-7-(5-ethyl-1,3,4-thiadiazol-2-yl)-8-methyl-8,9-dihydro-7H-1,3-dioxolo-[4,5-h][2,3]benzodiazepine | 142–144 (precipit. with water) | 47 −602° (c = 0.5, EtOH) |
| Method E | MS: EI(70 eV): [M]⁺: 407, m/z: 392, 279, 278, 253, 252 Cl: [M + H]⁺: 408, [M]⁺: 407 | | |
| 90 | (±)-5-(4-Aminophenyl)-8-methyl-7-(5-trifluoromethyl-1,3,4-thiadiazol-2-yl)-8,9-dihydro-7H-1,3-dioxolo-[4,5-h][2,3]benzodiazepine | 216–218 | 33 |
| Method A | ¹H NMR (CDCl₃) δ 1.39(3H, d, 6.5Hz), 2.80(1H, dd, 14.0Hz, 10.0Hz), 2.93(1H, dd, 14.0Hz, 5.0Hz), 4.06(2H, br), 5.28(1H, dm), 6.00(2H, dm), 6.61(1H, s), 6.69(2H, dm), 6.81 (1H, s), 7.48(2H, dm,) MS: EI(70 eV): [M]⁺: 447, m/z: 432, 279, 253, 252 CI: [M + H]⁺: 448, [M]⁺: 447, m/z: 252 | | |
| 91 | (±)-5-(4-Aminophenyl)-7-(5-phenyl-1,3,4-thiadiazol-2-yl)-8-methyl-8,9-dihydro-7H-1,3-dioxolo-[4,5-h][2,3]benzodiazepine | 228–230 (50% EtOH—H₂O) | 84 |
| Method A | ¹H NMR (DMSO-$d_6$) δ 1.28(3H, d, 6.5Hz), 2.67(1H, dd, 14.0Hz, 10.0Hz), 3.01(1H, dd, 14.0Hz, 5.0Hz), 5.02(1H, m), 5.81(2H, br), 6.07(2H, dm), 6.59(1H, s), 6.61(2H, dm), 7.08 (1H, s), 7.40(2H, dm), 7.45(3H, m), 7.81(2H, d) MS: EI(70 eV): [M]⁺: 455, m/z: 440, 295, 279, 253, 252 CI: [M + H]⁺: 456, [M]⁺: 455, m/z: 295 | | |
| 92 | (±)-5-(4-Aminophenyl)-7-(5-cyclopropylamino-methyl-1,3,4-thiadiazol-2-yl)-8-methyl-8,9-dihydro-7H-1,3-dioxolo[4,5-h][2,3]benzodiazepine | 135–138 | 35 |
| Method A | ¹H NMR (CDCl₃) δ 0.45(4H, m), 1.33(3H, d, 6.5Hz), 2.28(1H, m), 2.75(1H, dd, 14.0Hz, 9.9Hz), 2.85(1H, dd, 14.0Hz, 4.9Hz), 4.0(2H, br), 4.10(2H, s), 5.26(1H, m), 6.00(2H, m), 6.60(1H, s), 6.68(2H, dm), 6.80(1H, s), 7.49(2H, dm) | | |
| 93 | (±)-1-(4-Aminophenyl)-8-chloro-4-methyl-3-(1,3,4-thiadiazol-2-yl)-4,5-dihydro-3H-[2,3]benzodiazepine | 125–128 | 79 |
| Method A | ¹H NMR (DMSO-$d_6$) δ 1.18(3H, d, 6.5Hz), 2.69(1H, dd, 14.0Hz, 10.8Hz), 3.14(1H, dd, 14.0Hz, 5.1Hz), 5.05(1H, m), 5.83(2H, s), 6.62(2H, dm), 7.10(1H, s), 7.33(2H, dm), 7.51 (2H, m) | | |
| 94 | (±)-1-(4-Aminophenyl)-8-chloro-4-methyl-3-(5-methyl-1,3,4-thiadiazol-2-yl)-4,5-dihydro-3H-[2,3]benzodiazepine | 131–133 | 88 |

TABLE 10-continued 2,3-Benzodiazepines containing aminophenyl group
(The ¹H NMR spectra were recorded at 250 MHz unless stated otherwise)

| Number of Example | Name | Mp. (° C.) Solvent of recrystall. | Yield (%) [α]$_D$ |
|---|---|---|---|
| Method A | ¹H NMR (DMSO-d$_6$) δ 1.18(3H, d, 6.5Hz), 2.70(1H, dd, 14.0Hz, 10.3Hz), 3.11(1H, dd, 14.0Hz, 5.3Hz), 2.50(3H, s), 4.96(1H, m), 5.80(2H, s), 6.62(2H, dm), 7.10(1H, s), 7.32 (2H, dm), 7.51(2H, m) | | |
| 95 | (±)-5-(4-Amino-3-methylphenyl)-8-methyl-7-(5-methyl-1,3,4-thiadiazol-2-yl)-8,9-dihydro-7H-1,3-dioxolo-[4,5-h][2,3]benzodiazepine | 140–144 | 72 |
| Method B | MS: EI(70 eV): [M]⁺: 407, m/z: 392, 293, 266<br>CI: [M + H]⁺: 408, [M]⁺: 407, m/z: 266 | | |
| 96 | (±)-5-(3-Amino-4-methylphenyl)-8-methyl-7-(5-methyl-1,3,4-thiadiazol-2-yl)-7H-1,3-dioxolo-[4,5-h][2,3]benzodiazepine | 125 | 70 |
| Method B | ¹H NMR(500 MHz)(DMSO-d$_6$) δ 1.17(3H, d, 6.5Hz), 2.10(3H, s), 2.51(3H, s), 2.72(1H, dd, 14.1Hz, 9.1Hz), 3.05(1H, dd, 14.1Hz, 4.5Hz), 5.01(2H, s), 5.03(1H, m), 6.07(2H, dm), 6.55(1H, s), 6.70(1H, dd), 6.83(1H, d, 1.2Hz), 7.00(1H, d, 7.8Hz), 7.06(1H, s) | | |
| 97 | (±)-5-(3-Aminophenyl)-8-methyl-7-(5-methyl-1,3,4-thiadiazoyl-2-yl)-8,9-dihydro-7H-1,3-dioxolo-[4,5-h][2,3]benzodiazepine | 197–198 (iPrOH) | 77 |
| Method B, C | ¹H NMR(500 MHz)(DMSO-d$_6$) δ 1.17(3H, d, 6.5Hz), 2.51(3H, s), 2.77(1H, dd, 14.2Hz, 8.6Hz), 3.08(1H, dd, 14.2Hz, 4.3Hz), 5.06(1H, m), 5.24(2H, s), 6.07(2H, dm), 6.54(1H, s), 6.67(1H, d), 6.71(1H, d), 6.74(1H, d), 7.06(1H, s) | | |
| 98 | (±)-1-(4-Aminophenyl)-4-methyl-3-(5-methyl-1,3,4-thiadiazol-2-yl)-8-methoxy-4,5-dihydro-3H-[2,3]benzodiazepine | 180–184 | 84 |
| Method D | MS: EI(70 eV): [M]⁺: 379, m/z: 364, 265, 238, 223<br>CI: [M + H]⁺: 380, [M]⁺: 379, m/z: 223 | | |
| 99 | (±)-5-(4-Aminophenyl)-8-methyl-7-(5-methyl-6H-1,3,4-thiadiazin-2-yl)-8,9-dihydro-7H-1,3-dioxolo-[4,5-h][2,3]benzodiazepine | 154–157 | 85 |
| Method A | ¹H NMR (DMSO-d$_6$) δ 1.20(3H, d, 6.5Hz), 2.10(3H, s), 2.55(1H, dd, 14.0Hz, 11Hz), 2.92 (1H, dm), 2.92(1H, dd, 14.5Hz), 3.28(1H, d, 14.5Hz), 5.10(1H, m), 5.70(2H, s), 6.02(2H, dm), 6.55(2H, dm), 7.01(1H, s), 7.38(2H, dm), 7.60(1H, s) | | |
| 100 | (±)-5-(4-Aminophenyl)-7-(5,6-dihydro-5-oxo-4H-1,3,4-thiadiazin-2-yl)-8-methyl-8,9-dihydro-7H-1,3-dioxolo[4,5-h][2,3]benzodiazepine | 172–176 | 83 |
| Method A | ¹H NMR (DMSO-d$_6$) δ 1.16(3H, d, 6.5Hz), 2.49(1H, dd, 14.0Hz, 10.0Hz), 2.87(1H, dd, 14.0Hz, 5.2Hz), 3.31(2H, s), 4.78(1H, m), 5.68(2H, s), 6.05(2H, dm), 6.65(1H, s), 6.66 (2H, dm), 7.00(1H, s), 7.32(2H, dm), 10.5(1H, s) | | |
| 101 | (±)-5-(4-Aminophenyl)-8-methyl-7-(5-oxo-4,5-dihydro-1,3,4-thiadiazol-2-yl)-8,9-dihydro-7H-1,3-dioxolo-[4,5-h][2,3]benzodiazepine | 263–264 | 47 |
| Method C | ¹H NMR (DMSO-d$_6$) δ 1.17(3H, d, 6.5Hz), 2.58(1H, dd, 14.0Hz, 10.4Hz), 2.97(1H, dd, 14.0Hz, 5.4Hz), 4.71(1H, m), 5.65(2H, s), 6.04(2H, dm), 6.61(2H, dm), 6.62(1H, s), 7.01 (1H, s), 7.23(2H, dm), 11.81(1H, brs)<br>MS: EI(70 eV): [M]⁺: 395, m/z: 394, 306, 252<br>CI: [M + H]⁺: 396, [M]⁺: 395, m/z: 280 | | |
| 102 | (R)-5-(4-Aminophenyl)-8-methyl-7-(5-methyl-1,3,4-oxadiazol-2-yl)-8,9-dihydro-7H-1,3-dioxolo-[4,5-h][2,3]benzodiazepine | 145–149 | 86<br>−663°<br>(c = 0.5, EtOH) |
| Method A | MS: EI(70 eV): [M]⁺: 377, m/z: 252<br>CI: [M + H]⁺: 378, [M]⁺: 377, m/z: 252 | | |
| 103 | (±)-5-(4-Aminophenyl)-8-methyl-7-(2-methyl-3-oxo-2,3-dihydro-1,2,4-thiadiazol-5-yl)-8,9-dihydro-7H-1,3-dioxolo[4,5-h][2,3]benzodiazepine | 213 (EtOH) | 67 |
| Method A | ¹H NMR (DMSO-d$_6$) δ 1.23(3H, d, 6.5Hz), 2.70(1H, dd, 13.8Hz, 10.2Hz), 3.03(1H, dd, 13.8Hz, 4.2Hz), 3.06(3H, s), 4.91(1H, m), 5.90(2H, s), 6.08(2H, dm), 6.61(1H, s), 6.61 (2H, dm), 7.06(1H, s), 7.30(2H, dm) | | |
| 104 | (±)-5-(4-Aminophenyl)-7-(2-cyclopropyl-3-oxo-2,3-dihydro-1,2,4-thiadiazol-2-yl)-8-methyl-8,9-dihydro-7H-1,3-dioxolo[4,5-h][2,3]benzodiazepine | 265–267 | 82 |
| Method A | ¹H NMR (DMSO-d$_6$) δ 0.85(4H, m), 1.22(3H, d, 6.5Hz), 2.75(1H, dd, 14.0Hz, 10.0Hz), 2.75(1H, m), 3.02(1H, dd, 14.0Hz, 4.7Hz), 4.92(1H, m), 5.90(2H, s), 6.07(2H, dm), 6.60 (1H, s), 6.63(2H, dm), 7.04(1H, s), 7.30(2H, dm) | | |
| 105 | (±)-5-(4-Aminophenyl)-7-(2-ethyl-3-oxo-2,3-dihydro-1,2,4-thiadiazol-2-yl)-8-methyl-8,9-dihydro-7H-1,3-dioxolo[4,5-h][2,3]benzodiazepine | 212–214 | 59 |

TABLE 10-continued 2,3-Benzodiazepines containing aminophenyl group
(The $^1$H NMR spectra were recorded at 250 MHz unless stated otherwise)

| Number of Example | Name | Mp. (° C.) Solvent of recrystall. | Yield (%) [α]$_D$ |
|---|---|---|---|
| Method A | $^1$H NMR (CDCl$_3$) δ 1.25(3H, t), 1.27(3H, d, 6.5Hz), 2.80(1H, dd, 14.0Hz, 9.0Hz), 3.01 (1H, dd, 14.0Hz, 4.0Hz), 3.72(2H, q), 4.07(2H, br), 5.13(1H, m), 6.03(2H, dm), 6.65(1H, s), 6.67(2H, dm), 6.80(1H, s), 7.37(2H, dm) MS: EI(70 eV): [M]$^+$: 423, m/z: 408, 279, 252, 160 CI: [M + H]$^+$: 424, [M]$^+$: 423 | | |
| 106 | (±)-5-(4-Aminophenyl)-7-(4-carboxy-thiazol-2-yl)-8-methyl-8,9-dihydro-7H-1,3-dioxolo-[4,5-h][2,3]benzodiazepine | >260 (dec.) | 97 |
| Method A | MS: EI(70 eV): [M]$^+$: 422, m/z: 407, 279, 253 | | |
| 107 | (±)-5-(4-Aminophenyl)-8-methyl-7-(5-tetrazolyl)-8,9-dihydro-7H-1,3-dioxolo[4,5-h][2,3]benzodiazepine | >360 | 68 |
| Method A | MS: EI(70 eV): [M]$^+$: 363, m/z: 295, 294, 252 CI: [M + H]$^+$: 364, [M]$^+$: 363, m/z: 295 | | |
| 108 | (±)-5-(4-Aminophenyl)-8-methyl-7-(1,2,4-oxadiazol-3-yl)-7H-1,3-dioxolo-[4,5-h][2,3]benzodiazepine hydrochloride | 124–126 | 48 |
| Method A | MS: EI(70 eV): [M]$^+$: 363, m/z: 348, 253, 252 CI: [M + H]$^+$: 364, [M]$^+$: 363, m/z: 252 | | |
| 109 | (±)-5-(4-Aminophenyl)-8-methyl-7-(5-methyl-1,2,4-oxadiazol-3-yl)-8,9-dihydro-7H-1,3-dioxolo-[4,5-h][2,3]benzodiazepine | 130–135 | 74 |
| Method A | MS: EI(70 eV)(of the hydrochloride salt): [M]$^+$: 377, m/z: 362, 278, 252 CI: [M + H]$^+$: 378, [M]$^+$: 377, m/z: 252 | | |
| 110 | (±)-5-(4-Aminophenyl)-8-methyl-7-(2-methyl-thiazol-4-yl)-8,9-dihydro-7H-1,3-dioxolo-[4,5-h][2,3]benzodiazepine | 132–135 | 22 |
| Method C | MS: EI(70 eV): [M]$^+$: 392, m/z: 377, 279, 253, 252 CI: [M + H]$^+$: 393, [M]$^+$: 392 | | |
| 111 | (±)-5-(4-Aminophenyl)-8-methyl-7-(2-pyrimidinyl)-8,9-dihydro-7H-1,3-dioxolo[4,5-h][2,3]benzodiazepine | 233–235 (EtOH) | 96 |
| Method A | $^1$H NMR (DMSO-d$_6$) δ 1.23(3H, d, 6.5Hz), 2.50(1H, dd, 14.0Hz, 10.0Hz), 2.89(14.0Hz, 4.8Hz), 5.18(1H, m), 5.71(2H, s), 6.03(2H, dm), 6.58(2H, dm), 6.60(1H, s), 6.60(1H, t, 4.8Hz), 7.43(1H, s), 7.30(2H, dm), 8.33(2H, d, 4.8Hz) | | |
| 112 | (±)-5-(4-Aminophenyl)-7-(3-chloropyridazin-6-yl)-8-methyl-8,9-dihydro-7H-1,3-dioxolo-[4,5-h][2,3]benzodiazepine | 164–166 (EtOH) | 94 |
| Method A | MS: EI(70 eV): [M]$^+$: 407/409, m/z: 392/394, 355, 279, 278, 253, 252 CI: [M + H]$^+$: 408/410, [M]$^+$: 407/409, m/z: 279 | | |
| 113 | (±)-5-(4-Aminophenyl)-8-methyl-7-(1H(2H)-1,2,4-triazol-3-yl)-8,9-dihydro-7H-1,3-dioxolo-[4,5-h][2,3]benzodiazepine | 178–181 | 64 |
| Method A | MS: EI(70 eV): [M]$^+$: 362, m/z: 347, 279, 252 | | |
| 114 | (±)-5-(4-Aminophenyl)-8-methyl-7-(5-methyl-1H(2H)-1,2,4-triazol-3-yl)-8,9-dihydro-7H-1,3-dioxolo-[4,5-h][2,3]benzodiazepine | 166–169 | 72 |
| Method A | MS: EI(70 eV): [M]$^+$: 376, m/z: 361, 279, 252 | | |
| 115 | (±)-5-(4-Aminophenyl)-8-methyl-7-(2-methyl-2H-1,2,4-triazol-3-yl)-8,9-dihydro-7H-1,3-dioxolo-[4,5-h][2,3]benzodiazepine | 182–183 | 83 |
| Method A | MS: EI(70 eV): [M]$^+$: 376, m/z: 361, 279, 252 | | |
| 116 | (±)-5-(4-Aminophenyl)-8-methyl-7-(1-methyl-1H-1,2,4-triazol-3-yl)-8,9-dihydro-7H-1,3-dioxolo-[4,5-h][2,3]benzodiazepine | 165–168 | 83 |
| Method A | MS: EI(70 eV): [M]$^+$: 376, m/z: 361, 253, 252 | | |
| 117 | (±)-5-(4-Aminophenyl)-8-methyl-7-(2,5-dimethyl-2H-1,2,4-triazol-3-yl)-8,9-dihydro-7H-1,3-dioxolo-[4,5-h][2,3]benzodiazepine | 185–187 | 78 |
| Method A | MS: EI(70 eV): [M]$^+$: 390, m/z: 375, 279, 265, 252 | | |
| 118 | (±)-5-(4-Aminophenyl)-8-methyl-7-(1,5-dimethyl-1H-1,2,4-triazol-3-yl)-8,9-dihydro-7H-1,3-dioxol[4,5-h][2,3]benzodiazepine | 197–200 | 85 |
| Method C | MS: EI(70 eV): [M]$^+$: 390, m/z: 375, 253, 252 | | |
| 119 | (R)-5-(4-amino-3-methylphenyl)-8-methyl-7-(5-methyl-1,3,4-thiadiazol-2-yl)-8,9-dihydro-7H-1,3-dioxolo-[4,5-h][2,3]benzodiazepine | 158–160 | 83 −515° (c = 0.38, CHCl$_3$) |
| Method B | $^1$HNMR (DMSO-d$_6$) δ 1.18(3H, d, 5.4Hz), 2.07(s, 3H), 2.47(s, 3H), 2.57(dd, 1H, 13.7Hz, 10.3Hz), 2.95(dd, 1H, 13.7Hz, 4.9Hz), 4.92(m, 1H), 5.2–5.8(br, 2H), 6.01(s, br, 1H), 6.06 (s, br, 1H), 6.55(s, 1H), 6.64(d, 1H, 8.2Hz), 7.04(s, 1H), 7.17(d, 1H, 8.2Hz), 7.25(s, br, 1H) MS: EI(70 eV): [M]$^+$: 407, m/z: 392, 293, 278, 266 CI: [M + H]$^+$: 408, [M]$^+$: 407 | | |

Examples 120–131

General Procedure for the Synthesis of 2,3-benzodiazepines Containing acetylamino-phenyl Group 2,3-benzodiazepines containing an aminophenyl group were dissolved in dichloromethane and stirred at room temperature with an excess of acetic anhydride. After completion of the reaction the mixture was washed with sodium hydrogen carbonate solution and water, then dried and concentrated.

Equivalents

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

TABLE 11

2,3-benzodiazepine derivatives substituted with acetylaminophenyl group

| Number of Example | Name | Mp.(° C.) Solvent of recrystall. | Yield(%) $[\alpha]_D$ |
|---|---|---|---|
| 120 | (±)-5-(4-Acetylaminophenyl)-8-methyl-7-(5-methyl-thiazol-2-yl)-8,9-dihydro-7H-1,3-dioxolo-[4,5-h][2,3]benzodiazepine | 176–179 | 65 |
| 121 | (±)-5-(4-Acetylaminophenyl)-8-methyl-7-(4-methyl-thiazol-2-yl)-8,9-dihydro-7H-1,3-dioxolo-[4,5-h][2,3]benzodiazepine | 236–238 (50% EtOH—$H_2O$) | 65 |
| 122 | (±)-5-(4-Acetylaminophenyl)-7-(4,5-dihydro-thiazol-2-yl)-8-methyl-8,9-dihydro-7H-1,3-dioxolo-[4,5-h][2,3]benzodiazepine | 211–213 (EtOH) | 96 |
| 123 | (R)-5-(4-Acetylaminophenyl)-8-methyl-7-(2-thiazolyl)-8,9-dihydro-7H-1,3-dioxolo[4,5-h][2,3]benzodiazepine | 126(rearrangement) 172–174 (EtOH) | 95 −140° (c = 0.44, $CHCl_3$) |
| 124 | (S)-5-(4-Acetylaminophenyl)-8-methyl-7-(2-thiazolyl)-8,9-dihydro-7H-1,3-dioxolo-[4,5-h][2,3]benzodiazepine | 124–128 | 95 +134° (c = 0.48, $CHCl_3$) |
| 125 | (R)-5-(4-Acetylaminophenyl)-7-(4,5-dihydro-thiazol-2-yl)-8-methyl-8,9-dihydro-7H-1,3-dioxolo-[4,5-h][2,3]benzodiazepine | 143–145 | 95 +108° (c = 0.45, $CHCl_3$) |
| 126 | (S)-5-(4-Acetylaminophenyl)-7-(4,5-dihydro-thiazol-2-yl)-8-methyl-8,9-dihydro-7H-1,3-dioxolo-[4,5-h][2,3]benzodiazepine | 148–154 | 91 −111° (c = 048, $CHCl_3$) |
| 127 | (±)-5-(4-Acetylaminophenyl)-7-(4,5-dihydro-oxazol-2-yl)-8-methyl-8,9-dihydro-7H-1,3-dioxolo-[4,5-h][2,3]benzodiazepine | 124–128 | 44 |
| 128 | (±)-5-(4-Acetylaminophenyl)-8-methyl-7-(2-pyrimidinyl)-8,9-dihydro-7H-1,3-dioxolo-[4,5-h][2,3]benzodiazepine | 162–163 (EtOH) | 96 |
| 129 | (±)-5-(4-Acetylaminophenyl)-7-(3-chloro-pyridazin-6-yl)-8-methyl-8,9-dihydro-7H-1,3-dioxolo-[4,5-h][2,3]benzodiazepine | 164–170 | 78 |
| 130 | (R)-5-(4-Acetylaminophenyl)-8-methyl-7-(5-methyl-1,3,4-thiadiazol-2-yl)-8,9-dihydro-7H-1,3-dioxolo-[4,5-h][2,3]benzodiazepine | 276–277 (MeOH) | 73 −114° (c = 0.5, $CHCl_3$) |
| 131 | (±)-5-(4-Acetylamino-3-methylphenyl)-8-methyl-7-(5-methyl-1,3,4-thiadiazol-2-yl)-8,9-dihydro-7H-1,3-dioxolo[4,5-h][2,3]benzodiazepine | 258–262 | 63 |

What we claim is:

1. A compound of formula (I),

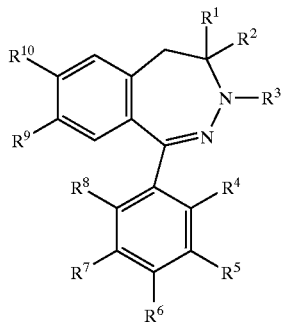

wherein:
$R^1$ and $R^2$ independently of each other represent hydrogen or $C_1$–$C_3$ alkyl, $R^3$ represents a substituted or unsubstituted 5- or 6-membered, aromatic, saturated or partially saturated heterocyclic ring having at least 2 heteroatoms selected from the group consisting of oxygen, sulfur and nitrogen, wherein the heterocyclic ring is optionally substituted with $C_1$–$C_5$ alkyl, $C_2$–$C_3$ alkenyl, $C_3$–$C_7$ cycloalkyl, trifluoromethyl, $C_1$–$C_3$ alkoxy, phenyl, formyl, carboxyl, $C_2$–$C_4$ alkoxycarbonyl, halogen or oxo, the $C_1$–$C_5$ alkyl or phenyl substituent being optionally substituted with halogen, $C_1$–$C_3$ alkoxy, alkylated amino or acylated amino, provided that when the heterocyclic ring has 2 heteroatoms, then one of the heteroatoms is different from nitrogen;

$R^4$, $R^5$, $R^6$, $R^7$ and $R^8$ independently from each other represent hydrogen, halogen, $C_1$–$C_3$ alkyl, nitro, or amino, wherein the amino is optionally substituted independently from each other with one or two $C_1$–$C_3$ alkyl, $C_2$–$C_5$ acyl, $C_2$–$C_5$ alkoxycarbonyl, aminocarbonyl, or $C_2$–$C_5$ alkylaminocarbonyl, $R^9$ represents $C_1$–$C_3$ alkoxy or halogen, $R^{10}$ represents hydrogen or halogen or $R^9$ and $R^{10}$ together are $C_1$–$C_3$ alkylenedioxy;

or a stereoisomer or pharmaceutically acceptable acid addition salt thereof.

2. A compound according to claim 1, wherein $R^3$ is selected from the group consisting of substituted and unsubstituted isoxazole, isothiazole, thiazole, thiazoline, 4-thiazolinone, oxazole, oxazoline, 1,3,4-thiadiazole, 1,3,4-thiadiazolin-2-one, 1,2,4-thiadiazolin-3-one, 1,4,2-oxathiazoline, 1,3,4-oxadiazole, 1,2,3-triazole, 1,3,4-triazole, tetrazole, 1,3-thiazin-4-one and 1,3,4-thiadiazin-4-one.

3. A compound according to claim 1, herein $R^3$ is a 1,3,4-thiadiazol-2-yl, a 4,5-dihydrothiazol-2-yl, a 2-thiazolyl or a 1,3,4-oxadiazolyl group, $R^5$ is hydrogen or methyl, $R^6$ is amino, and $R^9$ and $R^{10}$ represent together a methylenedioxy, or $R^9$ is chlorine or methoxy and $R^{10}$ is a hydrogen or chlorine.

4. A compound according to claim 1 selected from the group consisting of:
(R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(1,3,4-thiazol-2-yl)-8,9-dihydro-7H-1,3-dioxolo[4,5-h][2,3]benzodiazepine;
(R)-5-(4-aminophenyl)-8-methyl-7-(2-thiazolyl)-8,9-dihydro-7H-1,3-dioxolo[4,5-h][2,3]benzodiazepine:
(R)-5-(4-aminophenyl)-7-(4,5-dihydrothiazol-2-yl)-8-methyl-8,9-dihydro-7H-1,3-dioxolo[4,5-h][2,3]benzodiazepine;
(R)-5-(4-aminophenyl)-7-(5-ethyl-1,3,4-thiadiazol-2-yl)-8-methyl-8,9-dihydro-7H-1,3-dioxolo]4,5-h][2,3]benzodiazepine;
(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;
and the pharmaceutically acceptable acid addition salts thereof.

5. A pharmaceutical composition, corn rising a compound of formula (I) according to claim 1, or a stereoisomer or a pharmaceutically acceptable salt thereof, in a therapeutically effective amount, and a pharmaceutically acceptable carrier or vehicle therefor.

6. A method for treating glutamate hyperfunction in a disease selected from the group consisting of stroke, multiple sclerosis, essential tremor, Parkinson's disease, brain trauma and glaucoma and comprising administering to a subject in need of such treatment a therapeutically effective amount of a compound of claim 1.

7. A method for treating epilepsy comprising administering to a subject in need of such treatment a therapeutically effective antiepileptic amount of a compound of claim 1.

8. A method for reducing muscle spasms comprising administering to a subject in need of such treatment a therapeutically effective muscle relaxing amount of a compound of claim 1.

9. A method for treating an acute or chronic inflammatory disorder of the airways, comprising administering to a mammal in need of such treatment a therapeutically effective anti-inflammatory amount of a compound of claim 1.

10. The method of claim 9 wherein the inflammatory disorder of the airways treated is an allergic inflammatory disorder of the airways.

11. The method of claim 10 wherein the allergic inflammatory disorder of the airways is selected from the group consisting of allergic rhinitis, intrinsic asthma bronchiale, extrinsic asthma bronchiale, acute bronchitis, or chronic bronchitis, chronic obstructive pulmonary disease and pulmonary fibrosis.

12. A compound of formula (I):

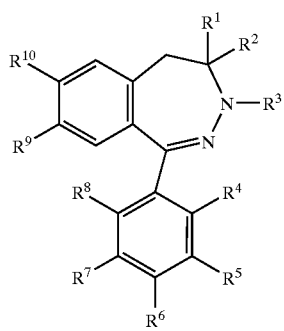

wherein:
$R^1$ and $R^2$ independently of each other represent hydrogen or $C_1$–$C_3$ alkyl;

R³ represents a heterocyclic ring selected from the group consisting of:
2-thiazolyl;
4-methylthiazol-2-yl;
5-methylthiazol-2-yl;
4,5-dimethylthiazol-2-yl;
4-phenylthiazol-2-yl;
4-ethoxycarbonylthiazol-2-yl;
4,5-dihydrothiazol-2-yl;
4,5-dihydro-4-oxothiazol-2-yl;
4,5-dihydro-5-methyl-4-oxothiazol-2-yl;
5,6-dihydro-4-oxo-4H-1,3-thiazin-2-yl;
4,5-dihydro-3-oxothiazol-2-yl;
4,5-dihydro-oxazol-2-yl;
1,3,4-thiadiazol-2-yl;
5-methyl-1,3,4-thiadiazol-2-yl;
5-cyclopropyl-1,3,4-thiadiazol-2-yl;
5-ethyl-1,3,4-thiadiazol-2-yl;
5-trifluoromethyl-1,3,4-thiadiazol-2-yl;
5-phenyl-1,3,4-thiadiazol-2-yl;
5-chloromethyl-1,3,4-thiadiazol-2-yl;
5-cyclopropylaminomethyl-1,3,4-thiadiazol-2-yl;
5-methyl-6H-1,3,4-thiadiazin-2-yl;
5,6-dihydro-5-oxo-4H-1,3,4-thiadiazin-2-yl;
5-oxo-4,5-dihydro-1,3,4-thiadiazol-2-yl;
5-methyl-1,3,4-oxadiazol-2-yl;
2-methyl-3-oxo-2,3-dihydro-1,2,4-thiadiazol-5-yl;
2-cyclopropyl-3-oxo-2,3-dihydro-1,2,4-thiadiazol-5-yl;
2-ethyl-3-oxo-2,3-dihydro-1,2,4-thiadiazol-5-yl;
4-carboxythiazol-2-yl;
5-tetrazolyl;
1,2,4-oxodiazol-3-yl;
5-methyl-1,2,4-oxadiazol-3-yl;
2-methylthiazol-4-yl;
(1H),(2H)-1,2,4-triazol-3-yl;
5-methyl-1H(2H)-1,2,4-triazol-3-yl;
2(1)H-1,2,4-triazol-3-yl;
2-methyl-2H-1,2,4-triazol-3-yl;
1,5-dimethyl-1H-1,2,4-triazol-3-yl;
1-methyl-1H-1,2,4-triazol-3-yl; and
2,5-dimethyl-2H-1,2,4-triazol-3-yl;
R⁴, R⁵, R⁶, R⁷ and R⁸ independently from each other represent hydrogen halogen, C₁–C₃ alkyl, nitro or amino, wherein the amino is optionally substituted independently from each other with one or two C₁–C₃ alkyl, C₂–C₅ acyl, C₂–C₅ alkoxycarbonyl, aminocarbonyl or C₂–C₅ alkylaminocarbonyl;
R⁹ represents C₁–C₃ alkoxy or halogen and R¹⁰ represents hydrogen or alogen, or R⁹ and R¹⁰ together are alkylenedioxy;
or a stereoisomer or pharmaceutically acceptable acid addition salt thereof.

13. The pharmaceutical composition according to claim 5, wherein the compound is selected from the group consisting of:
(R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(1,3,4-thiadiazol-2-yl)-8,9-dihydro-7H-1,3-dioxolo[4,5-h][2,3]benzodiazepine;
(R)-5-(4-aminophenyl)-8-methyl-7-(2-thiazolyl)-8,9-dihydro-7H-1,3-dioxolo[4,5-h][2,3]benzodiazepine;
(R)-5-(4-aminophenyl)-7-(4,5-dihydrothiazol-2-yl)-8-methyl-8,9-dihydro-7H-1,3-dioxolo[4,5-h][2,3]benzodiazepine;
(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;
(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;
and the pharmaceutically acceptable acid addition salts thereof.

14. The method according to claim 6, wherein the compound administered is selected from the group consisting of:
(R)-5-(4-amino-3-methylphenyl)-8-methyl-7-(5-methyl-1,3,4-thiadiazol-2-yl)-8,9-dihydro-7H-1,3-dioxolo(4,5-h][2,3]benzodiazepine;
(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(1,3,4-thiadiazol-2-yl)-8,9-dihydro-7H-1,3-7H-1,3-dioxolo[4,5-h][2,3]benzodiazepine;
(R)-5-(4-aminophenyl)-8-methyl-7-(2-thiazolyl)-8,9-dihydro-7H-13-dioxolo[4,5-h][2,3]benzodiazepine;
(R)-5-(4-aminophenyl)-7-(4,5-dihydrothiazol-2-yl)-8-methyl-8,9-dihydro-7H-1,3-dioxolo[4,5-h][2,3]benzodiazepine;
(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;
(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;
and the pharmaceutically acceptable acid addition salts thereof.

15. The method according to claim 7, wherein the compound administered is selected from the group consisting of:
(R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;
(R)-5-(4-aminophenyl)-8-methyl-7-(1,3,4-thiadiazol-2-yl)-8,9-dihydro-7H-1,3-dioxolo[4,5-h][2,3]benzodiazepine;
(R)-5-(4-aminophenyl)-8-methyl-7-(2-thiazolyl)-8,9-dihydro-7H-1,3-dioxolo[4,5-h][2,3]benzodiazepine;
(R)-5-(4-aminophenyl)-7-(4,5-dihydrothiazol-2-yl)-8-methyl-8,9-dihydro-7H-1,3-dioxolo[4,5-h][2,3]benzodiazepine;
(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;
(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;
and the pharmaceutically acceptable acid addition salts thereof.

16. The method according to claim 8, wherein the compound administered is selected from the group consisting of:
(R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(1,3,4-thiadiazol-2-yl)-8,9-dihydro-7H-1,3-dioxolo[4,5-h][2,3]benzodiazepine;

(R)-5-(4-aminophenyl)-8-methyl-7-(2-thiazolyl)-8,9-dihydro-7H-1,3-dioxolo[4,5-h][2,3]benzodiazepine;

(R)-5-(4-aminophenyl)-7-(4,5-dihydrothiazol-2-yl)-8-methyl-8,9-dihydro-7H-1,3-dioxolo[4,5-h][2,3]benzodiazepine;

(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;

(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;

and the pharmaceutically acceptable acid addition salts thereof.

17. The method according to claim 9, wherein the compound administered is selected from the group consisting of:

(R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(1,3,4-thiadiazol-2-yl)-8,9-dihydro-7H-1,3-dioxolo[4,5-h][2,3]benzodiazepine;

(R)-5-(4-aminophenyl)-8-methyl-7-(2-thiazolyl)-8,9-dihydro-7H-1,3-dioxolo[4,5-h][2,3]benzodiazepine;

(R)-5-(4-aminophenyl)-7-(4,5-dihydrothiazol-2-yl)-8-methyl-8,9-dihydro-7H-1,3-dioxolo[4,5-h][2,3]benzodiazepine;

(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;

(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;

and the pharmaceutically acceptable acid addition salts thereof.

18. The method according to claim 10, wherein the compound administered is selected from the group consisting of:

(R)-5-(4-amino-3-methylphenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(1,3,4-thiadiazol-2-yl)-8,9-dihydro-7H-1,3-dioxolo[4,5-h][2,3]benzodiazepine;

(R)-5-(4-aminophenyl)-8-methyl-7-(2-thiazolyl)-8,9-dihydro-7H-1,3-dioxolo[4,5-h][2,3]benzodiazepine;

(R)-5-(4-aminophenyl)-7-(4,5-dihydrothiazol-2yl)-8-methyl-8,9-dihydro-7H-1,3-dioxolo[4,5-h][2,3]benzodiazepine;

(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;

(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;

and the pharmaceutically acceptable acid addition salts thereof.

19. The method according to claim 11, wherein the compound administered is selected from the group consisting of:

(R)-5-(4-amino-3-methylphenyl)-8-methyl-7-(5-methyl-1,3,4-thiadizol-2-yl)-8,9-dihydro-7H-1,3-dioxolo[4,5-h][2,3]benzodiazepine;

(R)-5-(4-aminophenyl)-8-methyl-7-(5-methyl-1,3,4-thiadiazol-2-yl)-8,9-dihydro-7H-1,3-dioxolo[4,5-h][2,3]benzodiazepine;

(R)-5-(4-aminophenyl)-8-methyl-7-(1,3,4-thiadiazol-2-yl)-8,9-dihydro-7H-1,3-dioxolo[4,5-h][2,3]benzodiazepine;

(R)-5-(4-aminophenyl)-8-methyl-7-(2-thiazolyl)-8,9-dihydro-7H-1,3-dioxolo[4,5-h][2,3]benzodiazepine;

(R)-5-(4-aminophenyl)-7-(4,5-dihydrothiazol-2-yl)-8-methyl-8,9dihydro-7H-1,3-dioxolo[4,5-h][2,3]benzodiazepine;

(R)-5-(4-aminophenyl)-7-(5-ethyl-1,3,4-thiadiazol-2-yl)-8-methyl-8,9-dihydro-7H-1,3-dioxolo[4,5-h][2,3]benzodiazepine;

(R)-5-(4-aminophenyl)-8-methyl-7-(5-methyl-1,3,4-oxadiazol-2-yl)-8,9-dihydro-7H-1,3-dioxolo[4,5-h][2,3]benzodiazepine;

and the pharmaceutically acceptable acid addition salts thereof.

\* \* \* \* \*